United States Patent
Saito et al.

(10) Patent No.: US 6,456,868 B2
(45) Date of Patent: Sep. 24, 2002

(54) NAVIGATION APPARATUS AND SURGICAL OPERATION IMAGE ACQUISITION/DISPLAY APPARATUS USING THE SAME

(75) Inventors: Akito Saito, Hino; Takao Shibasaki, Tokyo; Takeo Asano, Kunitachi; Hiroshi Matsuzaki, Hachioji; Yukihito Furuhashi, Hachioji; Akio Kosaka, Hachioji, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/875,628

(22) Filed: Jun. 6, 2001

Related U.S. Application Data

(62) Division of application No. 09/533,651, filed on Mar. 22, 2000.

(30) Foreign Application Priority Data

Mar. 30, 1999 (JP) .......................................... 11-089405
Jun. 10, 1999 (JP) .......................................... 11-163964

(51) Int. Cl.[7] .............................................. A61B 5/055
(52) U.S. Cl. ........................ 600/429; 600/407; 600/113; 600/101; 606/130; 348/47; 348/72
(58) Field of Search ................................ 600/429, 407, 600/416, 417, 109, 117, 113, 160, 473, 476, 101, 110, 111, 118; 606/130; 378/62, 63; 348/45, 47, 72, 65, 79

(56) References Cited

U.S. PATENT DOCUMENTS 5,572,999 A * 11/1996 Funda et al.
5,638,819 A * 6/1997 Manwaring et al.

FOREIGN PATENT DOCUMENTS

| JP | 5-203881 | 8/1993 |
|---|---|---|
| JP | 7-261094 | 10/1995 |
| JP | 9-173352 | 7/1997 |
| JP | 10-5245 | 1/1998 |

OTHER PUBLICATIONS

Office Action (Final Rejection) dated Feb. 20, 2002 issued in parent application Ser. No. 09/533,651 filed Mar. 22, 2000—Inventors: Akito Saito et al (7 pages).

* cited by examiner

Primary Examiner—Marvin M. Lateef
Assistant Examiner—Runa Shah Qaderi
(74) Attorney, Agent, or Firm—Frishauf, Holtz, Goodman & Chick, P.C.

(57) ABSTRACT

A navigation apparatus comprises a navigation-related information generating section and a display section. The navigation-related information generating section measures the position and orientation of an object and a target in a three-dimensional space and generate navigation-related information to be used for navigating the object toward the target. The display section displays the navigation-related information generated by the navigation-related information generating section in any of different modes depending on the relationship of the position and orientation of the object and that of the target. A surgical operation image acquisition/display apparatus comprises an observation section, an image display section and a specifying section. The observation section includes a plurality of observation sections whose position and orientation is modifiable. The image display section is adapted to alternatively display any of the images obtained by the observation sections or synthetically combine and display the combined images. The specifying section specifies the image to be displayed to the image display section according to the position and orientation of the observation section.

15 Claims, 16 Drawing Sheets

DISTANCE MAP
EXPRESSES VARIABLES CORRESPONDING TO THE THREE-DIMENSIONAL
COORDINATE FOR THE SPACE CONTAINING THE TARGET IN TERMS OF
INDICES OF THE ARRAY $[x\ y\ z]^t$:COORDINATE OF POSITION ON MODEL DATA
xpitch:MINIMAL UNIT OF DIVISION OF X COORDINATE
ypitch:MINIMAL UNIT OF DIVISION OF Y COORDINATE
zpitch:MINIMAL UNIT OF DIVISION OF Z COORDINATE
dist[][][]:DISTANCE MAP
distance:THE DISTANCE FROM SURFACE OF THE TARGET
IN TERMS OF VALUES OF THE ARRAY

--- i=abs(x/xpitch)
j=abs(y/ypitch)
k=abs(z/zpitch)
dist[i][j][k]=distance
...
dist[0][0][0]=210
dist[1][0][0]=200
...
dist[256][256][256]=-20
...
dist[512][512][512]=280

FIG. 2

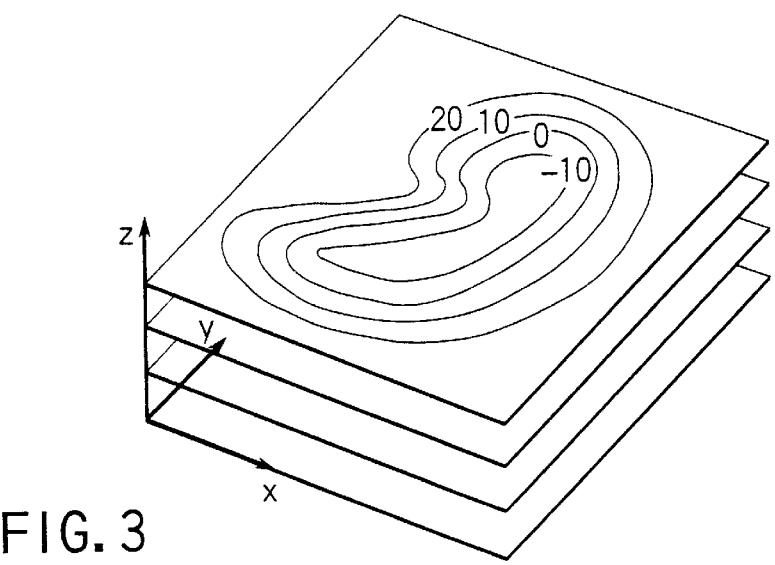

FIG. 3

(DISPLAY MODE 0)

MICROSCOPE IMAGE

FIG. 15A (DISPLAY MODE 1)

ENDOSCOPE IMAGE

FIG. 15B (DISPLAY MODE 2) | ENDOSCOPE IMAGE

MICROSCOPE IMAGE

FIG. 15C (DISPLAY MODE 3) | MICROSCOPE IMAGE

ENDOSCOPE IMAGE

FIG. 15D (DISPLAY MODE 4)

MICROSCOPE IMAGE

ENDOSCOPE IMAGE

FIG. 15E (DISPLAY MODE 5) | MICROSCOPE IMAGE

ENDOSCOPE IMAGE

FIG. 15F

NAVIGATION APPARATUS AND SURGICAL OPERATION IMAGE ACQUISITION/DISPLAY APPARATUS USING THE SAME

CROSS-REFERENCE TO RELATED APPLICATIONS

This application is a division of Ser. No. 09/533,651 filed Mar. 22, 2000.

This application is based upon and claims the benefit of priority from the prior Japanese Patent Applications No. 11-089405, filed Mar. 30, 1999; and No. 11-163964, filed Jun. 10, 1999, the entire contents of which are incorporated herein by reference.

BACKGROUND OF THE INVENTION

This invention relates to a navigation apparatus and, more particularly, to a navigation apparatus adapted to modify navigation-related information according to the relative position and orientation of the object of navigation and the target within a three-dimensional space.

This invention also relates to a surgical operation image acquisition/display apparatus and, more particularly, to an operation image acquisition/display apparatus adapted to acquisition and display images of a plurality of observation systems used in surgical operations.

Various navigation apparatus have been proposed for applications in the field of surgical operations, including those disclosed in Jpn. Pat. Appln. KOKAI Publication Nos. 9-173352 and 10-5245.

The medical navigation system disclosed in Jpn. Pat. Appln. KOKAI Publication No. 9-173352 is adapted to display information (profile information, medical image information) on the desired part of the object of examination specified by a specifying section for specifying a desired part of the object of examination.

It is also adapted to display video information obtained by an appearance imaging section, profile information on the profile measured by a profile measuring section and medical image information obtained by a medical image acquisition section on an image display section in an overlaid way.

The surgical operation assisting apparatus disclosed in Jpn. Pat. Appln. KOKAI Publication No. 10-5245 is adapted to display the current position of the surgical instrument being used in a surgical operation and the blood vessel located closest to the instrument on a tomographic image of the area of surgical operation in an overlaid manner by using the image data on the tomographic image, the surgical instrument being used, blood vessel detection section for detecting the blood vessel located closest to the surgical instrument, a position detection section for detecting the current position of the surgical instrument, an arithmetic computing section for computationally determines the position of the front end of the surgical instrument and the direction in which the surgical instrument is inserted, an image selection section for selecting the image data on the image being acquired for the area where the front end of the surgical instrument is located and an image synthesizing section for synthetically combining the image selected by the image selection section and a predetermined pattern indicating the front end of the surgical instrument in an overlaid manner.

The above described arrangement is intended to allow the operator to visually confirm the position of the front end of the surgical instrument inserted into the body of the patient on the tomographic image being displayed.

However, the medical navigation system and the surgical operation assisting apparatus as disclosed in the above patent documents are accompanied by the following problems.

As for the medical navigation system disclosed in Jpn. Pat. Appln. KOKAI Publication No. 9-173352, it simply displays information on a desired part of the object of examination specified by the section for specifying a desired part of the object of examination and it is difficult to navigate the section to the part desired by the user.

Additionally, this known medical navigation system provides a difficulty with which the surgeon realizes distances in the perspective of displayed information in the direction connecting the eyes of the surgeon and the display screen that is perpendicular to the latter.

Furthermore, this known medical navigation system provides an additional difficulty with which the surgeon determines the route of navigation on the basis of the displayed information when both the object of examination and the section for specifying the desired part of the object of examination are located at respective positions that are found within the measurable area but outside the displayable area of the system.

The surgical operation assisting system disclosed in Jpn. Pat. Appln. KOKAI Publication No. 10-5245 is accompanied by a problem of cumbersomeness that the user has to be constantly aware of the distance between the position of the front end of the surgical instrument on the displayed tomographic image and the position of the detected blood vessel in order to know the distance between the blood vessel and the surgical instrument.

In recent years, micro-surgery has become popular as a result of the development of both surgical techniques and surgical instruments.

In micro-surgery, generally a surgical microscope is used to observe an enlarged view of the area of surgical operation.

Particularly, in the field of cranial nerve surgery and otorhinolarygology, there arise occasions frequently where the area of operation can hardly be observed because it is at the so-called dead angle if the surgical microscope is handled elaborately when the area is located deep in the body.

For observing an area at such a dead angle, normally a mirror or an endoscope is used.

When using an endoscope for micro-surgery, it has to manipulated and placed accurately at the right position that is located deep in the body having an exquiarealy complicated three-dimensional structure because the area of operation is always at the dead angle of the surgical microscope.

The manipulation has to be conducted carefully by the operator, while observing it through the surgical microscope so that any normal tissues of the patient would not be inadvertently damaged by the endoscope and, at the same time, the area of operation has to be visually confirmed by means of the endoscope.

While manipulating the endoscope, the operator has to select instantaneously either the image taken by the surgical microscope or the image acquired by way of the endoscope as object of observation and the selection has to be correct.

As an attempt for aiding a surgeon manipulating the endoscope, Jpn. Pat. Appln. KOKAI Publication No. 5-203881 proposes an integrated image system comprising a plurality of CCD cameras connected to respective observation systems, each including a surgical microscope, an endoscope and other instruments, a CCD camera controller for controlling the operation of selectively using any of the observation systems and a view finder controller so that the user may select any of the observation systems by means of the CCD camera controller in the course of the ongoing surgical operation.

Jpn. Pat. Appln. KOKAI Publication No. 7-261094 discloses a surgical microscope with which the user can switch from the image of the surgical microscope to that of the endoscope or vice versa or overlay one on the other whenever necessary.

However, with the known technique disclosed in the above described Jpn. Pat. Appln. KOKAI Publication No. 5-203881, the operator has to carry out the switching or overlaid operation at the cost of a smooth progress of the ongoing surgical operation.

Additionally, while the above patent document describes that the image may be switched from one to the other, it does not describe specifically how the switching operation proceeds.

On the other hand, the known technique disclosed in Jpn. Pat. Appln. KOKAI Publication No. 7-261094 involves the use of a mode switch with which the surgical operator can switch the display mode whenever necessary.

However, it is highly cumbersome for the operator to switch from the image of the surgical microscope to that of the endoscope or vice versa when he or she has to place the endoscope in a position deep in the body of the patient having an exquiarealy complicated three-dimensional structure. Additionally, such a switching operation can obstruct the smooth progress of the surgical operation.

BRIEF SUMMARY OF THE INVENTION

In view of the above identified problems of the prior art, it is therefore the object of the present invention to provide a navigation apparatus with which the user can easily and visually realize the distance between a target and an object of navigation by modifying the obtained navigation-related information according to the relative position and orientation of the object of navigation and the target within a three-dimensional space and the user can easily obtain navigation-related information of the type necessary for the user.

Another object of the invention is to provide an operation image acquisition/display apparatus adapted to acquire and display images of a plurality of observation systems used in surgical operations without requiring the operator to manually switch from one observation system to another so that the ongoing surgical operation may proceed smoothly.

In the first aspect of the invention, the above first object is achieved by providing a navigation apparatus comprising:
  a navigation-related information generating section for generating navigation-related information by measuring the relative position and orientation of an object and a target in a three-dimensional space in order to navigate the object to the target; and
  a display section for displaying the navigation-related information generated by the navigation-related information generating section in different modes according to the relative position and orientation of the object and the target.

Thus, according to the invention, a navigation apparatus is provided that is adapted to display navigation-related information in different modes according to the relative position and orientation of the object and the target within a three-dimensional space.

A navigation apparatus according to the invention will be described hereinafter in terms of the first and second embodiments. While the above target may normally be a patient, a tumor to be surgically treated in a patient or an area of the body of a patient requiring special attention during a surgical operation, it is by no means limited to an existing object of examination and may alternatively be a virtual target displayed as a two-dimensional or three-dimensional image of a model synthesized by using the video information of an existing target that is obtained in advance.

While the above object may normally refer to an endoscope 3, it may alternatively refer to some other surgical instrument such as a suction pipe or a pair of forceps.

While the above display section may normally refer to a liquid crystal monitor, it may alternatively refer to some other video information display such as a CRT display or a head mount display.

For the purpose of the invention, the above expression "in different modes" refers to differences in color, in the thickness of line, in dimensions and in the density of drawing.

In the second aspect of the invention, the above second object is achieved by providing a surgical operation image acquisition/display apparatus comprising:
  an observation section having a plurality of observation section and adapted to modify its position and orientation;
  an image display section adapted to alternatively or synthetically display the images obtained by the plurality of observation section of the observation section; and
  an indication section for indicating the images to be displayed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a schematic illustration of a distance map that can be used for a navigation apparatus according to the invention;

FIG. 3 is a schematic illustration of a distance map that can be used for a navigation apparatus according to the invention;

FIGS. 9A through 9D schematically illustrate examples of images that may be displayed on a liquid crystal monitor, of which FIG. 9A is an image obtained by overlaid a wireframe image as navigation information on an image obtained by means of the optical system of an endoscope, FIG. 9B is an image obtained by overlaid an internal tomographic image of three-dimensional volume data as navigation information on an image obtained by means of the optical system of an endoscope, FIG. 9C is an image obtained when no target area is found within the effective area of measurement of an endoscope and FIG. 9D is an image obtained when the apparatus is inoperative for measurement;

FIGS. 15A through 15F are schematic illustrations of a plurality of display modes that can be realized by the video mixer 143 of FIG. 14;

DETAILED DESCRIPTION OF THE INVENTION

Figure 1:
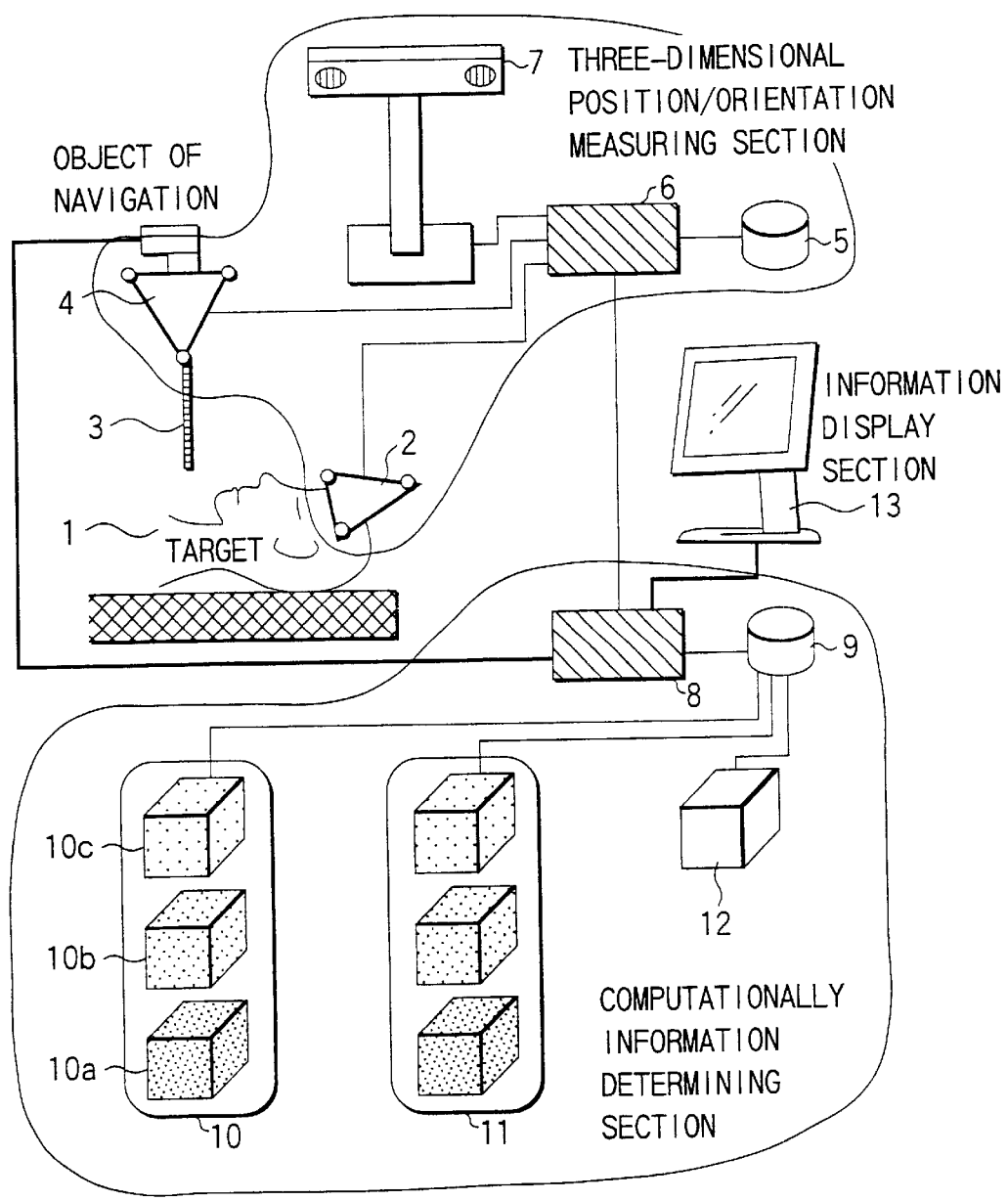
FIG. 1 is a schematic illustration of the first embodiment of the invention which is a navigation apparatus, showing its configuration.

Reference will now be made in detail to the presently preferred embodiments of the invention as illustrated in the several views of the accompanying drawing, in which like reference numerals designates like or corresponding parts.

Embodiment 1

FIG. 1 is a schematic illustration of the first embodiment of the invention which is a navigation apparatus, showing its configuration.

Referring to FIG. 1, object of examination 1, or patient, is lying flat on an operating table, facing upward.

A hard sensing plate 2 carrying three LEDs for emitting infrared rays that are arranged at the respective corners of a triangle is securely fitted to the head of the object of examination 1 in such a way that its position and orientation relative to the head would not change easily.

Another hard sensing plate 4 carrying three LEDs for emitting infrared rays arranged at the respective corners of a triangle is securely fitted to an endoscope 3.

The LEDs arranged on the sensing plate 2 and those arranged on the sensing plate 4 do not change their positional relationships.

The Positions of the LEDs of each of the sensing plates 2 and 4 are observed and determined in advance in terms of the coordinate system defined on the sensing plate and stored in sensor information storage section 5 as LED definition data.

The sensor information storage section 5 is connected to sensor control section 6.

Then, image acquisition type sensor assembly 7 is arranged at a position where the sensing plates 2 and 4 are found within its effective area of measurement.

Then, a three-dimensional position and orientation measuring section is established as the sensing plates 2 and 4 and the sensor assembly 7 are connected to sensor control section 6.

The three-dimensional position and orientation information obtained by the three-dimensional position and orientation measuring section is sent to navigation-related information control section 8.

The information including profile information and internal tomographic image information on the object of examination, the tumor thereof to be surgically treated and the parts thereof requiring special attention during a surgical operation and obtained in advance by measurement using CT and/or MRI is divided into low resolution information (e.g., for a resolution level of 32×32×32 voxels), medium resolution information (e.g., for a resolution level of 128×128×128 voxels) and high resolution information (e.g., for a resolution level of 512×512×512) and then transformed into wireframe three-dimensional model data 10 (high resolution wireframe three-dimensional model data 10a, medium resolution wireframe three-dimensional model data 10b, low resolution wireframe three-dimensional model data 10c) and three-dimensional volume data 11 (high resolution three-dimensional volume data 11a, medium resolution three-dimensional volume data 11b, low resolution three-dimensional volume data 11c) and stored in the navigation-related information storage section 9 as data.

The navigation-related information storage section 9 additionally stores in advance as distance map.

As shown in FIGS. 2 and 3, a distance map 12 contains a three-dimensional array having values representing the shortest distances from the surface of the target area (the object of examination, the tumor to be surgically treated or the parts of the body requiring special attention during a surgical operation), the affixed numbers of the array being variables corresponding to the three-dimensional positional coordinate system of the space where the target area is located.

For example, when the smallest unit of division is 0.1 mm, a 1/10 of an index number represents a corresponding coordinate value as expressed in terms of millimeter.

Assume that such a distance map is prepared for each target area in advance by means of a distance map preparing computer and stored in the navigation-related information storage section 9 as data.

Note that all the wireframe three-dimensional model data 10, the three-dimensional volume data 11 and the distance map 12 are subjected to a coordinate transforming operation so that they are be expressed in terms of a same coordinate system.

Then, the image obtained by way of the optical system of the endoscope 3 is taken into the navigation-related information control section 8 by way of a camera control unit and an image input board (not shown).

The navigation-related information generated by the navigation-related information control section 8 is displayed to the user on an information display section, which may be a liquid crystal monitor 13.

Figure 4:
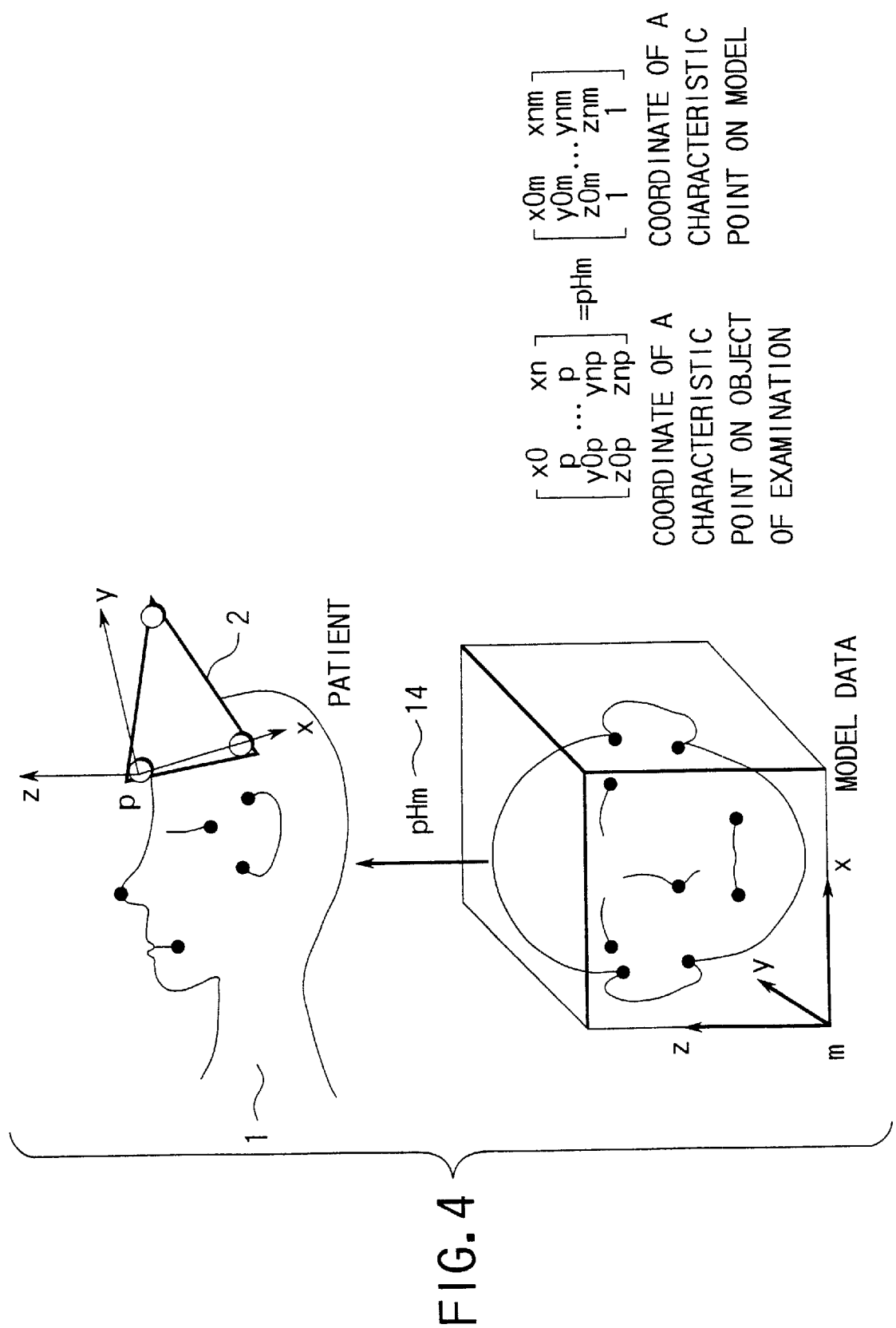
FIG. 4 is a schematic illustration of the relationship between data on an object of examination and the object of examination itself.

As shown in FIG. 4, data on the object of examination 1 and the object of examination 1 itself are correlated by measuring the coordinate value m of each characteristic point on the data and the coordinate values p of the corresponding characteristic point as defined by the sensing plate 2 and computing a coordinate transformation matrix (pHm) 14.

The coordinate transformation matrix (pHm) 14 is stored in the above navigation-related information storage section 9.

Figure 5:
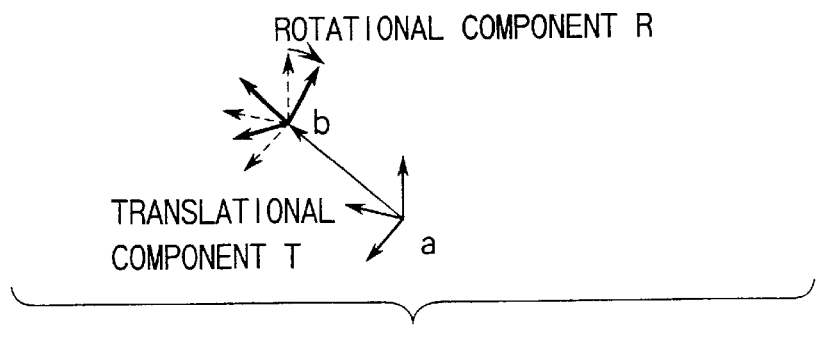
FIG. 5 is a schematic illustration of a coordinate transformation matrix for correlating data on an object of examination and the object of examination itself.

As shown in FIG. 5, a coordinate transformation matrix is a 4-row and 4-column matrix comprising a rotational component R representing a rotary motion in a three-dimensional space, a translational component T representing a translation in the three-dimensional space and a constant component.

Figure 6:
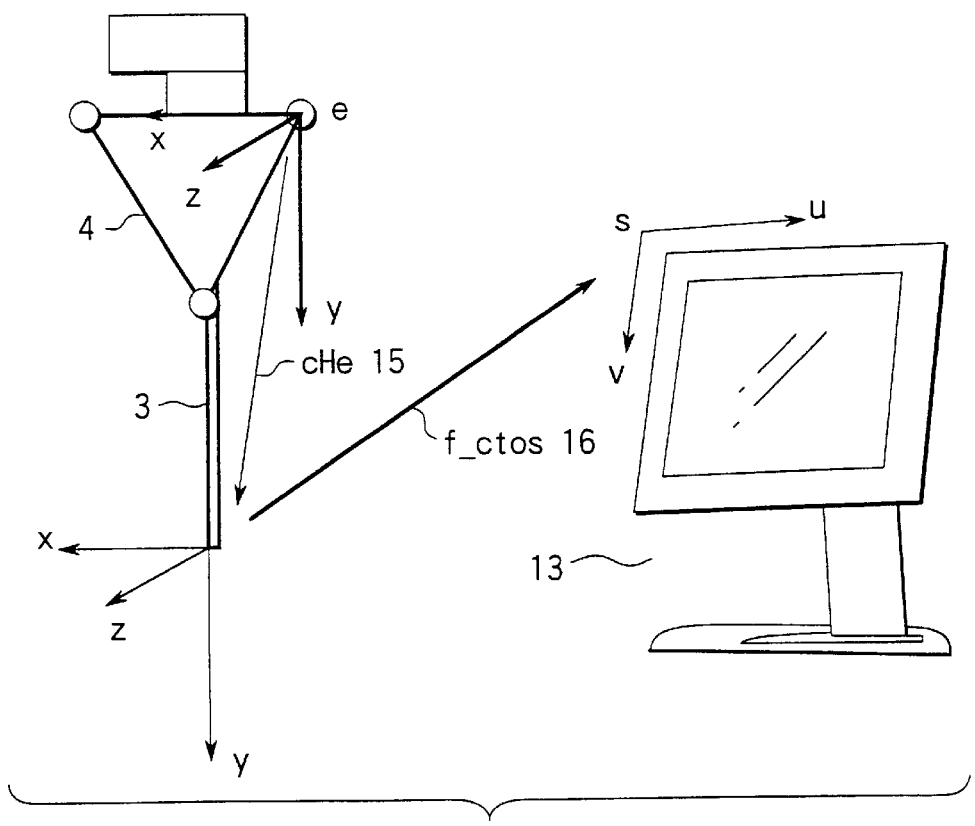
FIG. 6 is a schematic illustration of a coordinate transformation matrix for transforming a coordinate system defined by a sensing plate fitted to an endoscope into a coordinate system to be used by a camera model expressing the optical system of the endoscope and a coordinate transformation matrix for transforming the coordinate system of a camera model into the coordinate system of a liquid crystal monitor.

Additionally, as shown in FIG. 6 a coordinate transformation matrix (cHe) 15 for transforming the coordinate system defined by the sensing plate 4 into the coordinate system to be used by a camera model expressing the optical system of the endoscope 3 and a coordinate transformation matrix (f_ctos) 16 for transforming the camera model coordinate system into the coordinate system on the actual liquid crystal monitor 13 are also determined and stored in the navigation-related information storage section 9.

Now, the operation of the first embodiment of navigation apparatus according to the invention and having the above described configuration will be discussed below.

During the operation of the navigation apparatus, the sensor control section 6 that is a component of the three-dimensional position and orientation measuring section measures the three-dimensional position of each of the LEDs that are emitting infrared rays of the sensing plates 2 and 4 and then computationally determines the three-dimensional position and orientation information of each of the sensing plates 2 and 4 in terms of the coordinate values of the original point of the space defined by the sensing plate 4 on the three-dimensional space defined by turn by the sensing plate 2 and the values of the unit vectors along the X, Y and Z axis of the space defined by the sensing plate 4 by using the LED definition data stored in the sensor information storage section 5.

Figure 7:
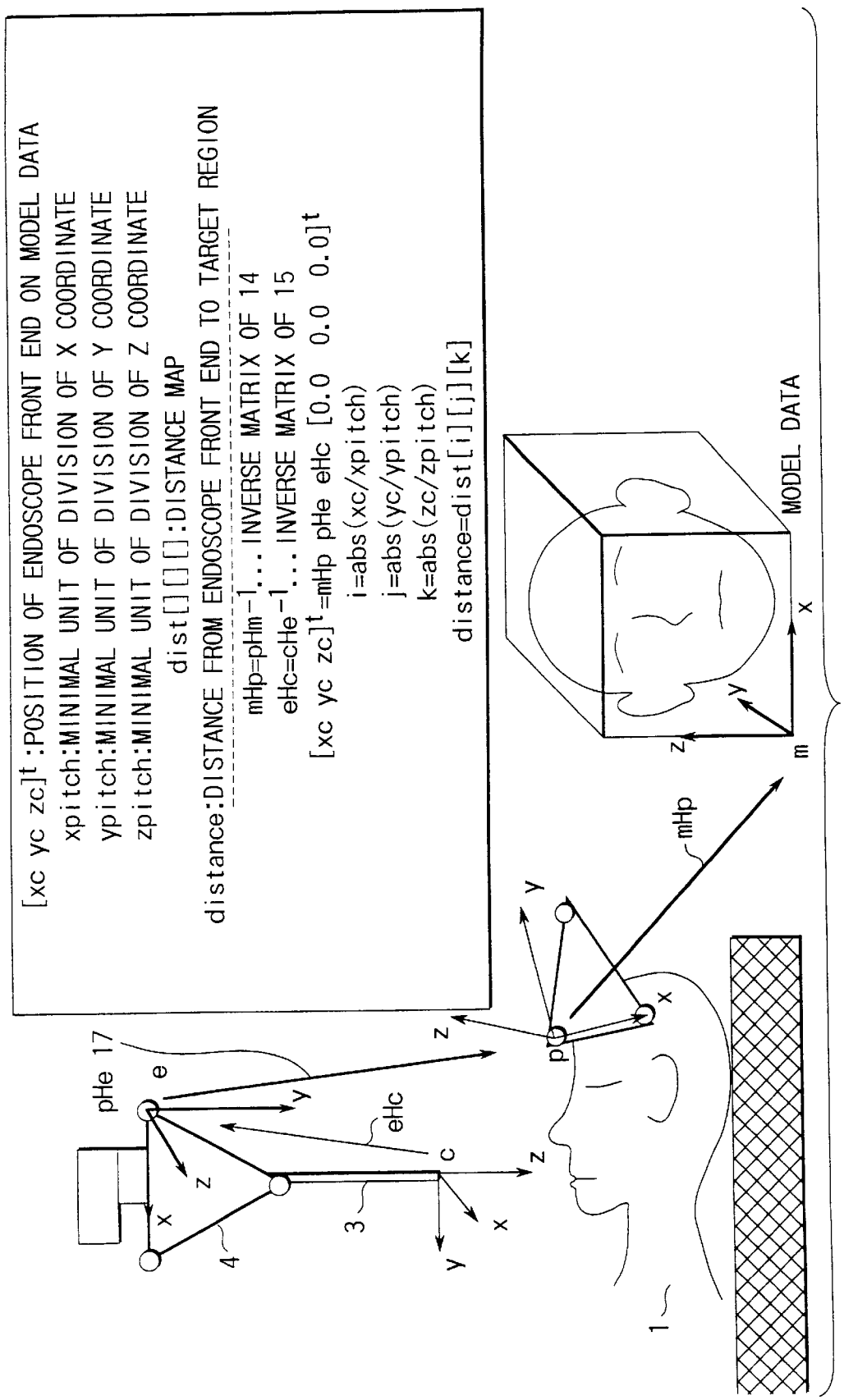
FIG. 7 is a schematic illustration of a coordinate transformation matrix for transforming a coordinate system defined by a sensing plate fitted to the head of an object of examination into the coordinate system defined by a sensing plate fitted to an endoscope.

Then, as shown in FIG. 7, the coordinate transformation matrix (pHe) 17 from the sensing plate 2 attached to the head of the object of examination 1 to the sensing plate 4 attached to the endoscope 3 is computationally determined on the basis of the obtained three-dimensional position and orientation information.

Figure 8:
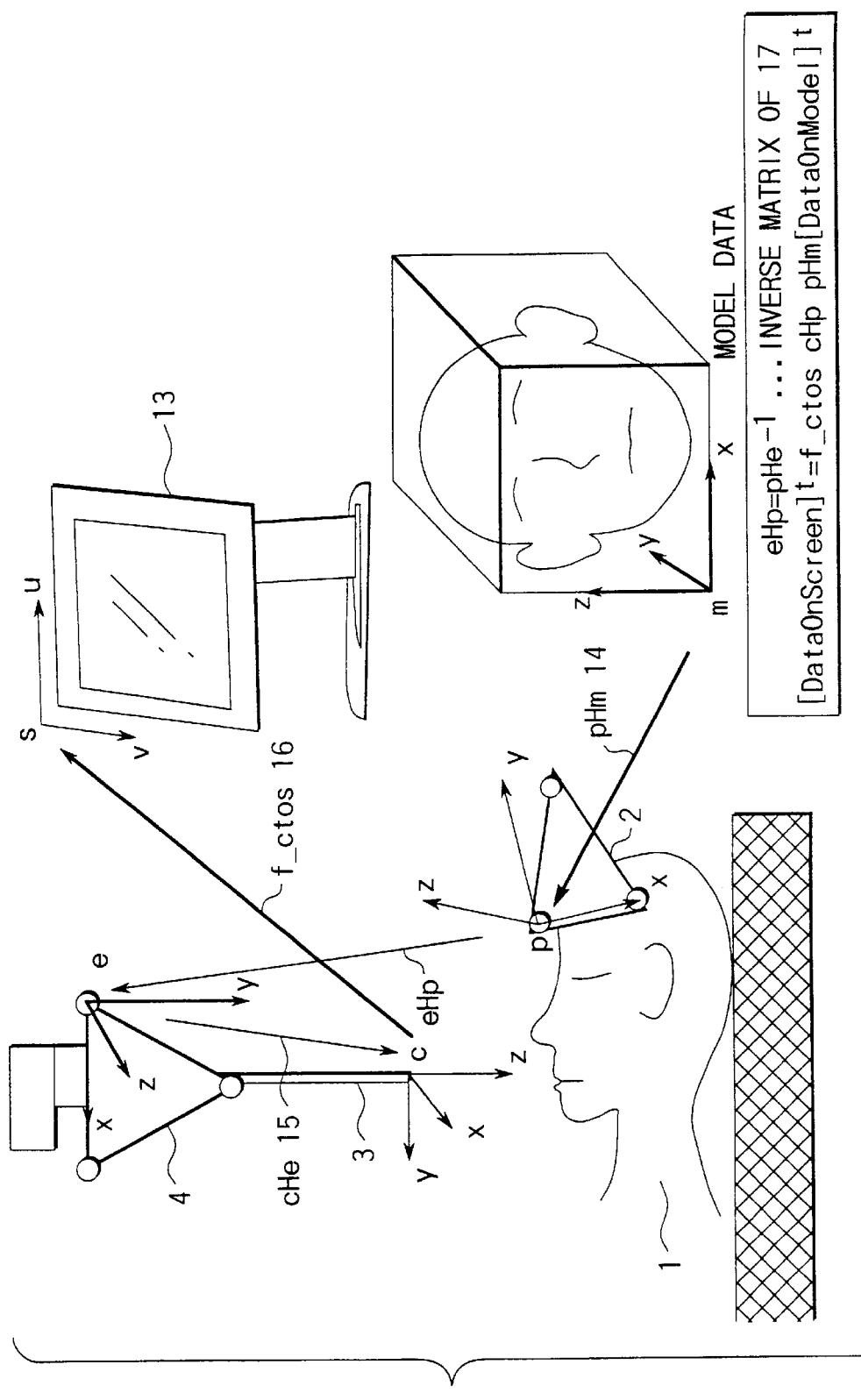
FIG. 8 is a schematic illustration of a transformation using a plurality of coordinate transformation matrices for transforming data on a target area into positional data on a liquid crystal monitor.

Then, as shown in FIG. 8, the data of target area is converted to the positional data on the liquid crystal monitor 13, the navigation-related information control sections 8 generates navigation-related information by using the obtained positional data based on the coordinate transformation matrix 17 and the coordinate transformation matrixes 14, 15 and 16.

Figure 9A:
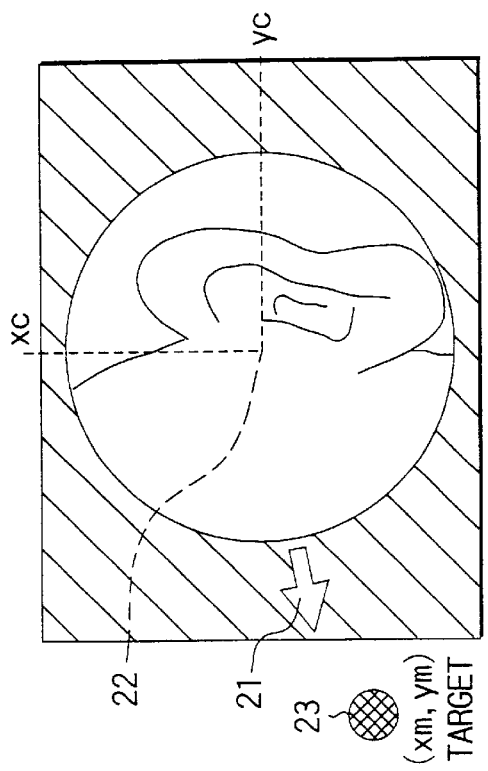

As the image formed by the optical system of the endoscope 3 is input to the navigation-related information control section 8, the navigation-related information and the image are displayed on the liquid crystal monitor 13 in an overlaid manner as shown in FIG. 9A.

Then, as shown in FIG. 7, the position of the front end of the endoscope 3 is subjected to an operation of coordinate transformation by using the above described coordinate transformation matrices 14, 15 and 17 and the relative distance between the target area and the front end of the endoscope 3 is determined by referring to the distance map 12.

Then, as shown in FIG. 9A, when the object of examination 1 and the endoscope 3 are in a measurable state, the relative distance between the target area and the front end of the endoscope 3 is displayed on the liquid crystal monitor 13 as the distance to the tumor in terms of the length of a bar 30 and a numerical value 31.

In a surgical operation using an endoscope 3, the endoscope 3 has to be inserted toward the tumor from the outside of the object of examination 1, paying attention to the parts that should not be damaged, and then the tumor has to be surgically treated.

When the endoscope 3 is located outside the object of examination 1, the model image of the target area is generated as a profiled, wireframe image 18 as shown in FIG. 9A.

In this embodiment, the color and the thickness of the lines of the wireframe image 18 are made to vary as a function of the relative distance between the front end of the endoscope 3 and the surface of the target area as determined in a manner as described above.

The color and the width of the bar 30 and those of the numerical value 31 showing the distance to the tumor are also made to vary along with those of the background.

For instance, when the relative distance is equal to or greater than 10 mm, the color of the lines of the wireframe image 18 may be blue and the thickness of the lines may be equal to 1 pixel while both the color of the bar 30 representing the distance and that of the background of the numerical value 31 may be equally blue and the width of the bar 30 may equal to 20 pixels.

When, on the other hand, the relative distance is equal to or greater than 0 mm and smaller than 10 mm, the color of the lines of the wireframe image 18 may be yellow and the thickness of the lines may be equal to 2 pixels while both the color of the bar 30 representing the distance and that of the background of the numerical value 31 may be equally yellow and the width of the bar 30 may equal to 30 pixels.

If the front end of the endoscope 3 is inserted by a distance equal to or greater than 0 mm and smaller than 10 mm, the color of the lines of the wireframe image 18 may be purple and the thickness of the lines may be equal to 2 pixel while both the color of the bar 30 representing the distance and that of the background of the numerical value 31 may be equally purple and the width of the bar 30 may equal to 30 pixels.

In this way, when the front end of the endoscope 3 has traveled by a predetermined distance, both the color of the wireframe image 18 and the thickness of the lines of the wireframe image 18 may be made to change so that the user can visually recognize the distance between the surface of the target area and the front end of the endoscope 3.

Additionally, the wireframe image 18 of an area requiring special attention may be drawn with thick lines when the endoscope 3 is located close to the area and separated therefrom by a distance smaller than a predetermined value so that the user may visually recognize that the endoscope 3 is too close to the area.

For instance, when the reference value of the distance map 12 for the area requiring special attention is less than 10 mm, the lines of the area requiring special attention of the wireframe image 18 may be made five times thicker than before.

The denseness or coarseness of the wireframe image 18 that is drawn in correspondence to the relative distance between the endoscope 3 and the surface of the target area is also made to vary.

More specifically, a set of more detailed wireframe three-dimensional model data 10a will be selected as the relative distance is reduced, whereas a set of more scarce wireframe three-dimensional model data 10c will be selected as the relative distance is increased.

For instance, high resolution wireframe three-dimensional model data 10a will be used when the distance to the target area is less than 30 mm and medium resolution wireframe three-dimensional model data 10b will be used when the distance to the target area is between 30 mm and 100 mm, whereas low resolution wireframe three-dimensional model data 10c will be used when the distance to the target area is greater than 100 mm.

With this arrangement, the problem of the prior art that coarse wireframe three-dimensional model data have to be used to reduce the time until the completion of drawing a wireframe image in order to save time when the endoscope is approaching the target area whereas dense wireframe three-dimensional model data are used to unnecessarily consume time before the completion of drawing a wireframe image when the endoscope is remote from the target area is successfully eliminated and a required level of detail and drawing rate can be realized depending on the distance between the endoscope and the target area.

Figure 9C:
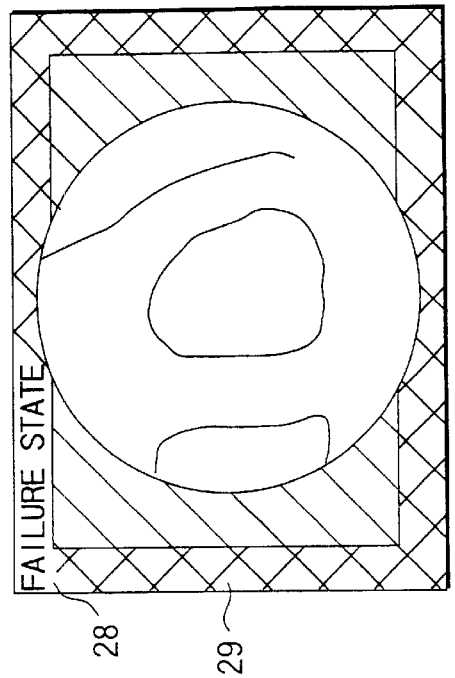
Figure 9B:
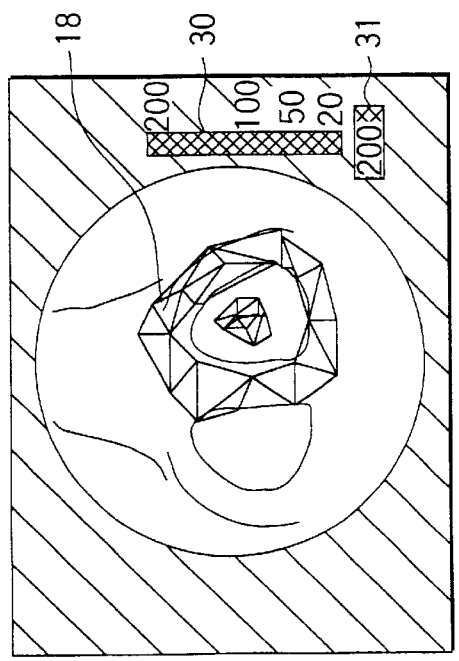

Additionally, when the endoscope 3 is inserted into the object of examination 1 by using the above described embodiment, the model image of the object of examination 1 drawn by the embodiment is switched from the wireframe image 18 to the internal tomographic image 19 obtained by using the three-dimensional volume data of the object of examination 1 as shown in FIG. 9B depending on the relative distance between the endoscope 3 and the outermost zone of the target area.

The relative distance between the front end of the endoscope 3 and the surface of the target is determined in a manner as described above.

For instance, the model image of the object of examination may be switched from the wireframe image 18 to an internal tomographic image 19 obtained by using the three-dimensional volume data of the object of examination that reflect the viewing direction of the endoscope.

As a result of this switching operation, the user can easily acquire the internal tomographic image 19 that is very important after the insertion of the endoscope 3 instead of the wireframe image 18 of the object of examination that becomes unnecessary after the insertion of the endoscope 3 without being required to carrying out the switching operation by him or herself.

Thus, the navigation-related information displayed to the user when the endoscope 3 is inserted into the object of examination includes the internal tomgraphic image obtained by using the three-dimensional volume data of the object of examination 1 and the wireframe image 20 of the area requiring special attention.

As the endoscope 3 is brought close to the target and separated from the latter by a distance smaller than a predetermined value under this condition, not only the drawing attributes of the wireframe image 20 but also the color of the internal tomographic image 19 drawn by using the three-dimensional volume data are made to change.

If, on the other hand, the target is not found within the effective area of measurement of the endoscope 3, arrow 21 indicates the direction in which the target area will be found as shown in FIG. 9C.

If the model image is found within the drawable (displayable) range or not can be determined by checking if the coordinate of each and every point of the model image as computed when drawing the model image is found as a point on the monitor to be used for displaying the image.

Figure 10:
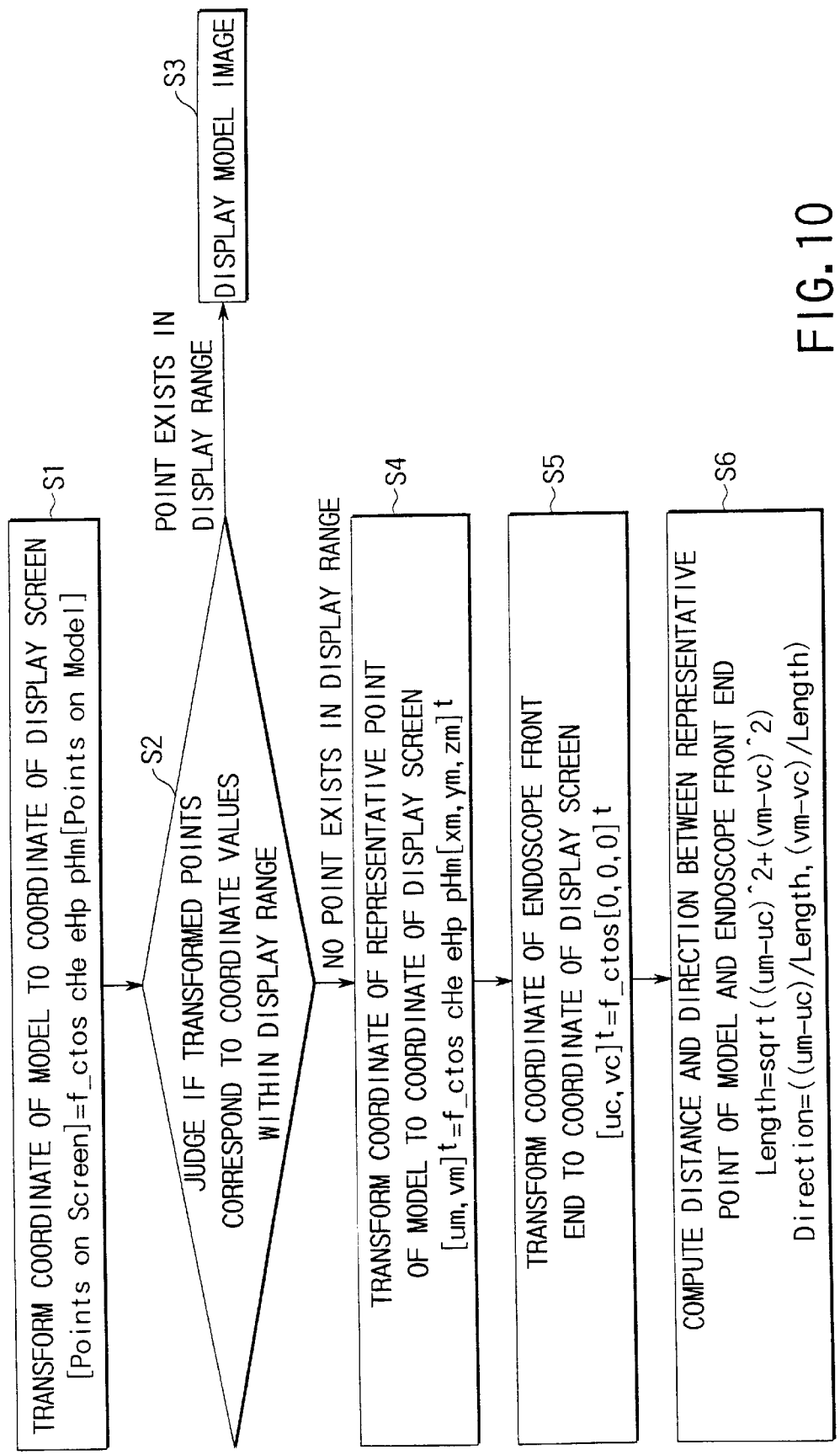
FIG. 10 is a flow chart of a display operation for displaying an image as shown in FIG. 9C.

Referring to FIG. 10, the coordinate of the model image is transformed into the coordinate of the display screen (Step S1) and it is determined if the coordinate of a transformed point is found within the displayable range of the display screen (Step S2).

If the coordinate is found within the displayable range, the model image is displayed on the screen (Step S3).

If, on the other hand, the coordinate is not found within the display range, the coordinate of a representative point of the model image is transformed into the corresponding coordinate of the display screen (Step S4) and, at the same time, the coordinate of the front end of the endoscope 3 is transformed into the corresponding coordinate of the display screen (Step S5). Then, the distance and the direction of the line connecting the representative point of the model image and the front end of the endoscope 3 are computationally determined (Step S6).

Thus, the relative distance and the relative direction of the line connecting the center 22 of the endoscope image, or the front end of the endoscope 3, and the target can be determined by transforming the coordinate values 23 on the model data coordinate system of the representative point of the target into the coordinate values on the liquid crystal monitor 13 by means of the above described coordinate transformation matrices 14, 15, 16 and 17.

Then, the user can visually comprehend the extent to which the endoscope 3 should be moved to bring the target into the effective area of measurement of the endoscope 3 by modifying the size of the arrow 21 indicating the target area in proportion to the obtained distance.

When the apparatus is incapable of measuring the distance and the direction, the sensor control section 6 outputs a message telling the user that the apparatus is incapable of measuring the distance and the direction in place of three-dimensional position and orientation information.

Figure 9D:
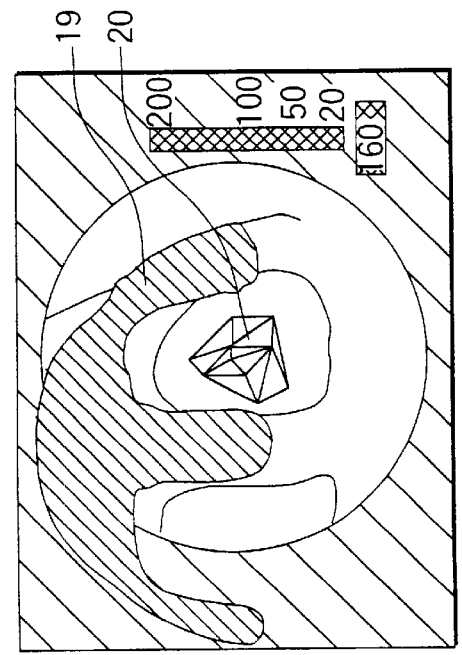

Upon receiving this message, the navigation-related information control section 8 erases the model image being displayed as navigation-related information and generates character information 28 of "unmeasurable condition" and a yellow pixel frame 29 having a width equal to 60 pixels, which are then displayed to the user on the liquid crystal monitor 13 as shown in FIG. 9D.

Then, the user can easily comprehend that the endoscope 3 or the object of examination 1 located at a position that makes the intended measurement impossible so that the user can be effectively protected against the risk of operating the endoscope 3 in a wrong way according to navigation-related information that does not reflect reality.

It is needless to say that the configuration of this embodiment can be modified and/or altered in various different ways.

For instance, the area that provides the object of navigation is not limited to the target area and may alternatively be a plurality of any areas which are defined by information on the profile of the object of examination 1 or information on an internal tomographic image.

It is also possible to carry out a simulation by fitting a sensing plate to the head of a virtual object of examination without using an actual object of examination 1.

The three-dimensional position and orientation measuring section may be made to alternatively comprises a magnetic sensor or a set of mechanical links and joints, encoders and potentiometers popularly used in ordinary three-dimensional position and orientation measuring systems.

When the object of examination is immobile, it is sufficient to measure the three-dimensional position and orientation of the object of examination 1, store the information in the sensor information storage section and utilize it in the computational operation for determining the relative three-dimensional position and orientation of the object of examination and the object of navigation in advance so that it is only necessary to measure the three-dimensional position and orientation of the object of navigation when the system is in operation.

The wireframe for expressing the profile information of the target area may be replaced by any known technique for graphic expression that is popularly used for three-dimensional computer graphics including polygons.

Alternatively, contour lines and equidistant curves relative to the viewing direction may be used.

The endoscope 3 that is the object of navigation may be replaced by a plurality of endoscopes.

The object of navigation may be a surgical instrument that is not provided with a section of observation.

The technique used for determining if the target area is located within the effective area of measurement or not is limited to the above described one.

The technique for determining the relative distance between the object of navigation and the target area is not limited to the above described one that uses a distance map and any known technique for computationally determining the distance between two points in a three-dimensional space may alternatively be used for determining the distance between a representative point of the object of navigation and a representative point of the target area for the purpose of the invention.

Additionally, the color may be made to change continuously as a function of the distance instead of the above described use of a single boundary value. Alternatively, the color may be made to change stepwise by providing a plurality of boundary values.

Similarly, the line thickness may be made to change continuously in stead of the above described use of a single boundary value. Alternatively, the line thickness may be made to change stepwise by providing a plurality of boundary values.

A situation where there is no navigation-related information to be displayed may be indicated by making the color to be transparent and the lines to be practically invisible.

The density of lines for drawing the model image that varies as a function of the distance may be made to change continuously on the basis of a single set of data instead of selectively using a plurality of sets of data with different levels of density that are provided in advance as described above.

The pattern that is displayed when the target area is out of the effective area of measurement is not limited to the arrow 21. Alternatively, a triangle, a circle, a bar or some other figure may be used. The distance may be expressed by the size of the figure.

Furthermore, the size of the arrow 21 may be made to vary stepwise by using a plurality of preselected values instead of making it vary continuously in a manner as described above.

When a section for determining the density of lines for drawing the model image of the target area on the basis of a single set of data is provided, it is no longer necessary to store in advance a plurality of sets of data with different levels of density.

The navigation-related information indicating a situation where the apparatus is incapable of measuring the distance and the direction may not require both character information 28 and a frame 29. It may be sufficient to use only either character information 28 or a frame 29 to convey the information.

It may be so arranged that the user can define the color and the line thickness that are used as attributes of the navigation-related information, the density of lines for drawing the model image, the size of the displayed pattern, the boundary values for changing the color and the line thickness as a function of the distance and the character string of the characteristic information 28 indicating that the incapability of measurement of the apparatus.

Embodiment 2

Now, the second embodiment of the invention, which is a navigation apparatus, will be discussed below.

Figure 11:
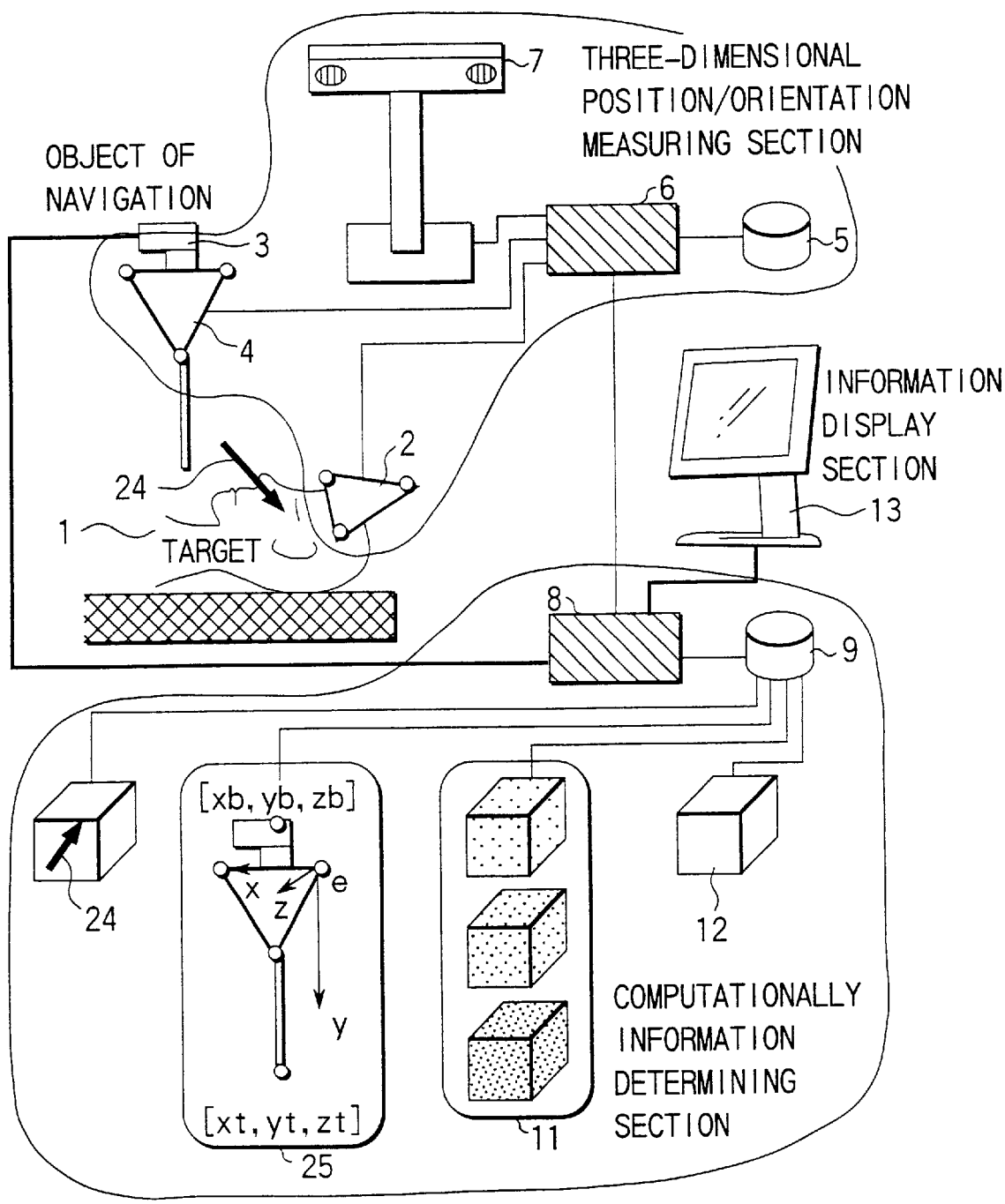
FIG. 11 is a schematic illustration of the second embodiment of the invention which is also a navigation apparatus, showing its configuration.
Figure 12:
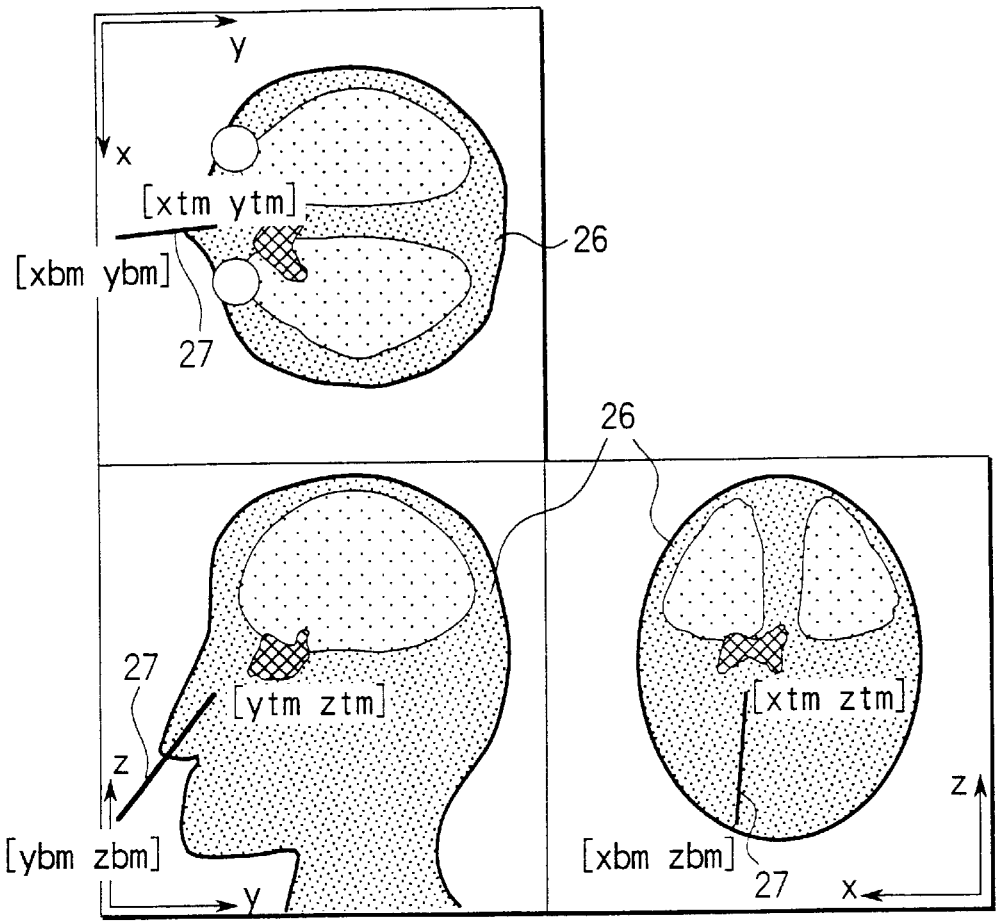
FIG. 12 is a schematic illustration of an example of an image displayed by the second embodiment and a coordinate transformation matrix that can be used for the display.
Figure 13:
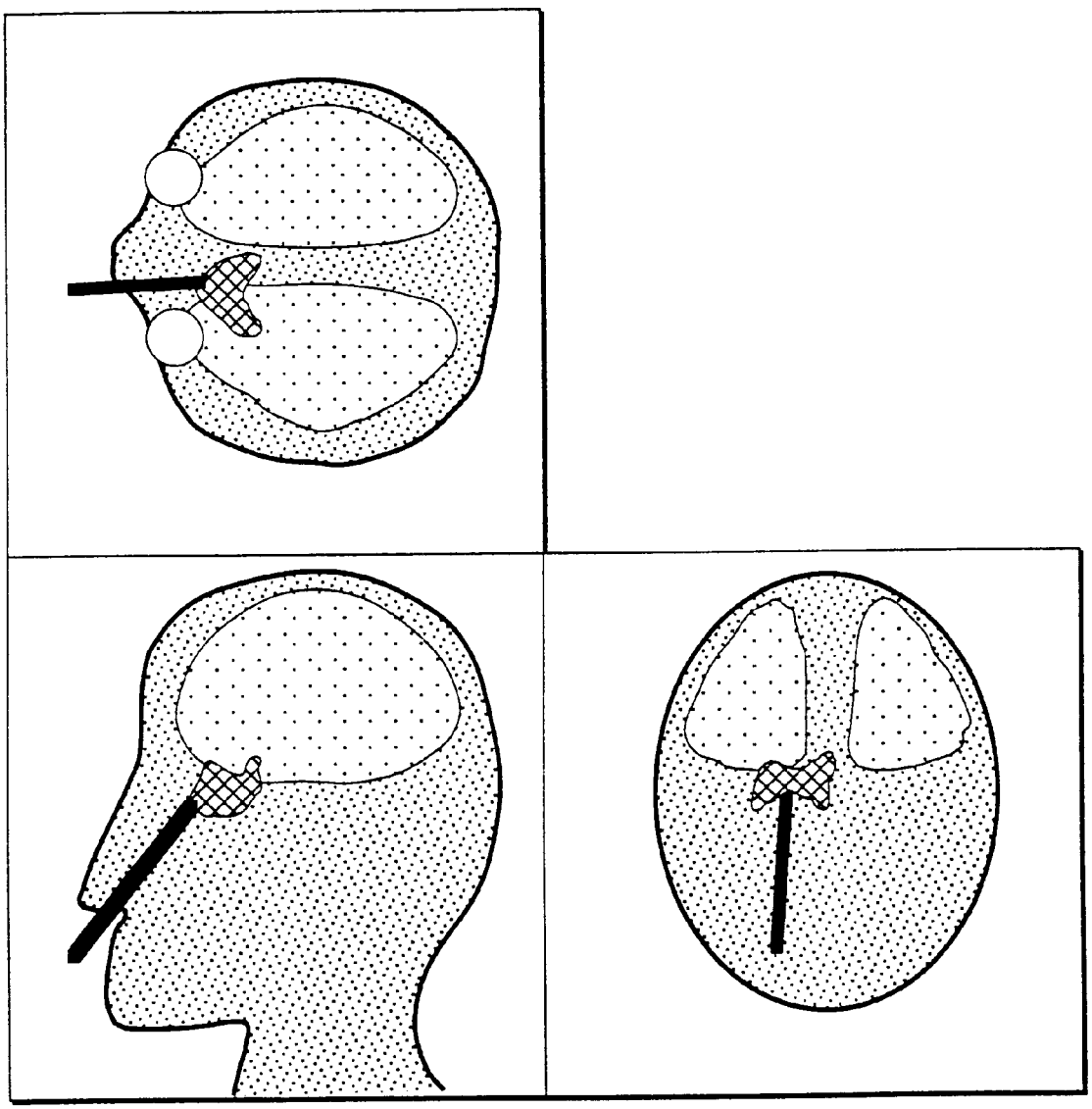
FIG. 13 is a schematic illustration of an operation of modifying the thickness of lines of an orthogonally projected image of an endoscope as a function of the relative distance between the target area and the front end of an endoscope.

FIG. 11 is a schematic illustration of the second embodiment of the invention which is also a navigation apparatus, showing its configuration.

This second embodiment has a configuration same as the above described first embodiment except the following.

In this embodiment, the endoscope 3 is not required to pass the imaging information obtained by the optical system to the navigation-related information control section 8.

In this embodiment, the navigation-related information storage section 9 stores in advance vectors 24 for expressing the route along which the endoscope 3 is inserted (minimal invasive route) as data.

Then, the coordinate values 25 for the front end and the rear end of the endoscope 3 are determined in terms of the coordinate system defined by the sensing plate 4 rigidly fitted to the endoscope 3 and stored in the navigation-related information storage section 9.

Now, the operation of the embodiment having the above described configuration will be described below.

When the embodiment of navigation apparatus is in operation, the sensor control section 6 measures the three-dimensional position of each of the LEDs that are emitting infrared rays of the sensing plates 2 and 4 and then computationally determines the three-dimensional position and orientation of each of the sensing plates 2 and 4, by using the LED definition data stored in the sensor information storage section 5.

Then, the coordinate transformation matrix 17 from the sensing plate 2 fitted to the head of the object of examination 1 to the sensing plate 4 fitted to the endoscope 3 is computationally determined on the basis of the obtained three-dimensional position and orientation information.

Then, the position and the orientation of the endoscope 3 is determined in terms of the data on the target area by using the coordinate transformation matrix 17 and the above described coordinate transformation matrices 14, 15.

Then, the navigation-related information control section 8 generates a tri-sectional image 26 of the three-dimensional volume data 11 including those of the tumor and an orthogonal projection image 27 of the endoscope 3 projected on the cross section as navigation-related information and displays it on the liquid crystal monitor 13.

If, for instance, the coordinate of a representative point of the tumor is expressed by (260, 180, 280), the tri-sectional image 26 of the three-dimensional volume data 11 will have a YZ plane with x=260, a ZX plane with y=180 and an XY plane with z=280.

Then, the relative distance between the surface of the target area and the front end of the endoscope 3 is determined by referring to the above described distance map 12, using the position of the front end of the endoscope 3.

The thickness of the lines of the orthogonal projection image 27 of the endoscope 3 is continuously changed as a function of the distance between the surface of the target area and the front end of the endoscope 3.

Then, the user can easily comprehend a situation where the endoscope 3 is approaching the target area.

The orientation of the endoscope 3 determined by the coordinate values 25 of the position of the front end and that of the rear end of the endoscope 3 is compared with the data of the vector indicating the direction in which the endoscope 3 is to be inserted and, if the orientation is inclined relative to the vector by a predetermined value (e.g., 10 degrees), the color and the line thickness of the orthogonal projection image 27 of the endoscope 3 will be changed.

Thus, the user can easily comprehend that the direction in which the endoscope 3 is currently inserted is deviating from the direction in which it is to be inserted.

It may be needless to say that the configuration of this embodiment can be modified and/or altered in various different ways.

For instance, the area that provides the object of navigation is not limited to the target area and may alternatively be a plurality of any areas which are defined by information on the profile of the object of examination 1 or information on an internal tomographic image.

It is also possible to carry out a simulation by fitting a sensing plate to the head of a virtual object of examination without using an actual object of examination 1.

The three-dimensional position and orientation measuring section may be made to alternatively comprise a magnetic sensor or a set of mechanical links and joints, an encoder and a potentiometer popularly used in ordinary three-dimensional position and orientation measuring systems.

When the object of examination is immovable, it is sufficient to measure the three-dimensional position and orientation of the object of examination 3, store the information in the sensor information storage section and utilize it in the computational operation for determining the relative three-dimensional position and orientation of the object of examination and the object of navigation in advance so that it is only necessary to measure the three-dimensional position and orientation of the object of navigation when the system is in operation.

The endoscope 3 that is the object of navigation may be replaced by a plurality of endoscopes.

While the above object of navigation may normally refer to an endoscope 3, it may alternatively refer to some other surgical instrument such as a suction pipe or a pair of forceps so long as the mechanical profile thereof can be determined by measurement.

The coordinate of the front end of the endoscope 3 does not need to agree with the actual front end and data may be manipulated to make the endoscope 3 virtually have an extended front end.

Alternatively, the coordinate of the front end of the endoscope 3 may be defined by means of an operational formula using the extension of the front end from the actual front end as parameter so that the coordinate of the front end may be determined successively on the basis of the extension specified by the user.

Additionally, the color may be made to change on the basis of a single boundary value instead of making it change continuously as a function of the distance in a manner as described above. Alternatively, the color may be made to change stepwise by providing a plurality of boundary values.

Similarly, the line thickness may be made to change on the basis of a single boundary value in stead of making it change continuously in a manner as described above. Alternatively, the line thickness may be made to change stepwise by providing a plurality of boundary values.

The technique of determining the angle of inclination of the endoscope 3 is not limited to the one described above.

It may be so arranged that the user can define the color and the line thickness that are used as attributes of the navigation-related information, the density of lines for drawing the model image, the size of the displayed pattern, the boundary values for changing the color and the line thickness as a function of the distance and the character string of the characteristic information 28 indicating that the incapability of measurement of the apparatus.

The object of navigation may be a microscope.

Then, position of the focal point can be defined as object of navigation by obtaining the focal length of the microscope from the microscope main body and replacing the coordinate of the front end of the endoscope 3 by that of the focal point.

While a navigation apparatus according to the invention is described above in terms of the first and second embodiments, the present invention is by no means limited thereto and the embodiments can be modified and/or altered in various different ways without departing from the scope of the present invention.

With a navigation apparatus according to one aspect of the present invention, a model image of the object or the target, information on the direction of navigation and/or information on the distance between the object of navigation and the target are displayed whenever the position and orientation of the object in a three-dimensional space can be determined so that the user can easily comprehend the position and orientation of the object of navigation in the three-dimensional space.

Additionally, when the apparatus is incapable of measuring the position and orientation, it displays so and, therefore, the user can easily be aware of the situation.

More specifically, while the above target may normally be a patient, a tumor to be surgically treated of a patient or an area of the body of a patient requiring special attention during a surgical operation, it is by no means limited to an existing object of examination and may alternatively be a virtual target displayed as a two-dimensional or three-dimensional image of a model synthesized by using the video information of an existing target that is obtained in advance.

While the above object may normally refer to an endoscope 3, it may alternatively refer to some other surgical instrument such as a suction pipe or a pair of forceps.

While the above display section may normally refer to a liquid crystal monitor, it may alternatively refer to some other video information display such as a CRT display or a head mount display.

While the above model image refers to wireframe model data 10 in the first embodiment, it may alternatively refer model data adapted to express a profile, including a popular data structure to be used for three-dimensional computer graphics.

Additionally, while the above model image refers to the three-dimensional volume data 11 of the target area in the first and second embodiments, it may alternatively take a form where a plurality of two-dimensional pixel data exist.

While the above described information on the direction of navigation refers to the arrow 21 in the first embodiment, it may alternatively be a two-dimensional geometric figure such as a triangle or a circle, a three-dimensional geometric figure such a cone or a set of visually recognizable image data.

While the above described distance information refers to the numeral 31 indicating the distance to the tumor in the first embodiment, it may alternatively be a numeral indicating the distance to an appropriate target.

While it also refers to the bar 30 indicating the distance to the tumor in the first embodiment, it may alternatively be a two-dimensional geometric figure such as a triangle or a circle, a three-dimensional geometric figure such a cone or a set of visually recognizable image data.

While the information indicating an unmeasurable condition refers to the character information 28 of "unmeasurable condition" in the first embodiment, it may alternatively include any character information telling the user that the apparatus is in an unmeasurable condition.

While it also refers to a yellow pixel frame 29 having a width equal to 60 pixels in the first embodiment, it may alternatively refer to any expression using symbols defined to indicate an unmeasurable condition.

With a navigation apparatus according to another aspect of the present invention, an image of an object acquired by the imaging section is displayed with other information on the object in an overlaid manner so that the user can obtain an actual image of the object and navigation-related information simultaneously and hence comprehend the position, the profile and the condition of the object that he or she cannot see on the basis of the navigation-related information.

While the object refers to the endoscope 3 in the first embodiment, it may alternatively refer to a microscope or some other object.

While the above display section normally refers to the liquid crystal monitor in the first embodiment, it may alternatively refer to some other video information display such as a CRT display or a head mount display.

With a navigation apparatus according to another aspect of the present invention, the relative position and orientation of the target and those of the object in a three-dimensional space are measured by means of a three-dimensional position and orientation measuring section.

Then, the information generating section of the navigation apparatus generates information necessary for navigating the object on the basis of the outcome of the measurement of the three-dimensional position and orientation measuring section.

Then, the display section of the navigation apparatus displays navigation-related information in a display mode selected out of a plurality of different display modes according to at least any of distance information on the distance between the object and the target, direction information on the direction of the target as viewed from the object or information telling if the object or the target is found within the effective area of measurement of the three-dimensional position and orientation measuring section or not.

As a result, the user can easily comprehend the distance between the target and the object, the direction of the target as viewed from the object and if the object or the target is found within the effective area of measurement of the three-dimensional position and orientation measuring section or not.

Thus, while the target is a patient 1, a tumor to be surgically treated of a patient or an area of the body of a patient requiring special attention during a surgical operation in the above first and second embodiments, it is by no means limited to an existing object of examination and may alternatively be a virtual target displayed as a two-dimensional or three-dimensional image of a model synthesized by using the video information of an existing target that is obtained in advance.

While the above object refers to an endoscope 3, it may alternatively refer to some other surgical instrument such as a suction pipe or a pair of forceps.

While the above three-dimensional position and orientation measuring section refers to sensors using LEDs for emitting infrared rays (sensing plates 2, 4, sensor assembly 7, sensor information storage section 5 and sensor control section 6), it may alternatively refer to a sensing system using magnetic sensors or a sensing system using a set of mechanical links and joints, an encoder and a potentiometer popularly used in ordinary three-dimensional position and orientation measuring systems.

The information generating section refers to the navigation-related information storage section 9 and the navigation-related information control section 8.

While the display section normally refers to the liquid crystal monitor 13, it may alternatively refer to some other video information display such as a CRT display or a head mount display.

For the purpose of the invention, the expression of "a plurality of different display modes" refers to differences in color, in the thickness of line, in the dimensions of the drawing and in the density of drawing lines.

With a navigation apparatus according to another aspect of the present invention, a display section displays at least profile information on the target or the object, internal tomographic information on the object, information on the direction of the object as viewed from the object or vice versa or information on the distance to the object when the target or the object is measurable by the three-dimensional position and orientation measuring section but it displays information telling that neither the target nor the object can be measured.

More specifically, while the above profile information refers to wireframe model data 10 in the first embodiment, it may also refer to model data adapted to express a profile, including a popular data structure to be used for three-dimensional computer graphics.

Additionally, while it refers to the lines drawing the orthogonal projection image 27 of the endoscope 3 in the second embodiment, it may also refer to expression techniques adapted to express a profile, including a popular data structure to be used for three-dimensional computer graphics.

Still additionally, while the internal tomographic information refers to the three-dimensional volume data 11 of the target area in the first and second embodiments, it may alternatively take a form where a plurality of two-dimensional pixel data exist.

While the above described direction of the target refers to the arrow 21 in the first embodiment, it may alternatively be a two-dimensional geometric figure such as a triangle or a circle, a three-dimensional geometric figure such a cone or a set of visually recognizable image data.

While the above described distance information refers to the numeral 31 indicating the distance to the tumor in the first embodiment, it may alternatively be a numeral indicating the distance to an appropriate target.

While it also refers to the bar 30 indicating the distance to the tumor in the first embodiment, it may alternatively be a two-dimensional geometric figure such as a triangle or a circle, a three-dimensional geometric figure such a cone or a set of visually recognizable image data.

While the information indicating an unmeasurable condition refers to the character information 28 of "unmeasurable condition" in the first embodiment, it may alternatively include any character information telling the user that the apparatus is in an unmeasurable condition.

While it also refers to a yellow pixel frame 29 having a width equal to 60 pixels in the first embodiment, it may alternatively refer to any expression using symbols defined to indicate an unmeasurable condition.

With a navigation apparatus according to another aspect of the present invention, the object has an imaging section and the image acquired by the imaging section is displayed with other navigation-related information obtained by the information generating section in an overlaid manner.

Thus, the user can obtain an actual image of the object and navigation-related information simultaneously and hence comprehend the position, the profile and the condition of the object that he or she cannot see on the basis of the navigation-related information.

While the object having an imaging section refers to the endoscope 3 in the first embodiment, it may alternatively refer to a microscope or some other object.

While the above display section normally refers to the liquid crystal monitor 13 in the first embodiment, it may alternatively refer to some other video information display such as a CRT display or a head mount display.

With a navigation apparatus according to another aspect of the present invention, the navigation-related information displayed on the display section changes its color as a function of the relative distance between the target and the object as measured by the three-dimensional position and orientation measuring section so that the user can visually comprehend with ease a situation where the relative distance is made too small.

Alternatively, it may be so arranged that both the relative distance and the direction toward the target as viewed from the object are evaluated at the same time and the color of the displayed information is changed depending on the situation. Then, the user can visually comprehend both the relative distance and the direction with ease.

More specifically, while the color of the displayed navigation-related information refers to that of the wireframe image 18 of the target area and the internal tomographic image 19 displayed on the monitor in the first embodiment, it may also refer to the color of the arrow 21 of the first embodiment.

It may additionally refers to the color of the tri-sectional image 26 of the target area and the orthogonal projection image 27 of the endoscope 3 in the second embodiment.

With a navigation apparatus according to another aspect of the present invention, the thickness of the lines of the navigation-related information displayed on the display section changes as a function of the relative distance between the target and the object as measured by the three-dimensional position and orientation measuring section so that the user can visually comprehend with ease a situation where the relative distance is made too small.

Additionally, as the thickness of the lines of the navigation-related information displayed on the display section changes as a function of the direction of the target as viewed from the object, the user can visually comprehend with ease a situation where the relative direction is deviating from the right direction.

Alternatively, it may be so arranged that both the relative distance and the direction toward the target as viewed from the object are evaluated at the same time and the line thickness of the displayed information is changed depending on the situation. Then, the user can visually comprehend both the relative distance and the direction with ease.

More specifically, while the line thickness of the displayed navigation-related information refers to that of the wireframe image 18 of the target area and the internal tomographic image 19 displayed on the monitor in the first embodiment, it may also refer to the line thickness of the arrow 21 of the first embodiment.

It may additionally refers to line thickness of the tri-sectional image 26 of the target area and the orthogonal projection image 27 of the endoscope 3 in the second embodiment.

With a navigation apparatus according to another aspect of the present invention, the profile model of the target and the internal tomographic image are switched from one to the other on the display section as a function of the relative distance between the target and the object as measured by the three-dimensional position and orientation measuring section so that the user can visually comprehend with ease that the object is located close to the target.

Thus, the user can get necessary information with ease depending on if the distance between the object and the target is smaller than a predetermined value or not.

More specifically, while the above profile model refers to wireframe image 18 in the first embodiment, it may also refer to various profiles used in three-dimensional computer graphics such as polygon as well as contour lines and equidistant curves drawn relative to the viewing direction. The above internal tomographic image refers to the internal tomographic image 19 of the first embodiment.

With a navigation apparatus according to another aspect of the present invention, the density of lines drawing the target model image is finely lowered when the relative distance between the target and the object is large and finely raised when the relative distance is small so as to make the load of drawing the target image and the quantity of information used for displaying the image may be well balanced.

As a result, the user can obtain an adequate amount of information that is displayed with an adequate drawing rate depending as a function of the relative distance between the target and the object.

More specifically, while the above profile model refers to wirefrane image 18 in the first embodiment, it may also refer to various profiles used in three-dimensional computer graphics such as polygon as well as contour lines and equidistant curves drawn relative to the viewing direction.

With a navigation apparatus according to another aspect of the present invention, the information generating section computationally determines the positional relationship of the image to be displayed and the display area of the display section on the basis of the relative distance between the target and the object and the relative direction of the target as viewed from the object and simply indicates the direction of the target when no image is displayed in the display area for the target so that the user can comprehend the relative positions of the target and the object and the direction of the target as viewed from the object without missing either of them by selecting the display of the direction when no image is displayed for the target.

More specifically, while the above profile model refers to wireframe image 18 in the first embodiment, it may also refer to various profiles used in three-dimensional computer graphics such as polygon as well as contour lines and equidistant curves drawn relative to the viewing direction along with information on the internal tomographic image.

While the above described information on the direction of navigation refers to the arrow 21 in the first embodiment, it may alternatively be a two-dimensional geometric figure such as a triangle or a circle, a three-dimensional geometric figure such a cone or a set of visually recognizable image data.

With a navigation apparatus according to another aspect of the present invention, the relative distance between the target and the object is indicated by the size or the shape of a symbol so that the user can visually comprehend with ease not only the distance but also the direction of the target as viewed from the object.

More specifically, while the above described symbol refers to the arrow 21 in the first embodiment, it may alternatively be a two-dimensional geometric figure such as a triangle or a circle, a three-dimensional geometric figure such a cone or a set of visually recognizable image data.

With a navigation apparatus according to another aspect of the present invention, the relative distance between the target and the object of navigation and their orientations in a three-dimensional space are determined by the three-dimensional position and orientation measuring section.

Then, an computational information determining section generates navigation-related information such as information three-dimensional position and orientation information on the target and the object of navigation including the relative distance between the target and the object of navigation and their orientations and if they are measurable or not and controls the generated information.

Then, the information display section displays the navigation-related information generated by the computational information determining section.

As a result, the user can easily comprehend the positional relationship between the target and the object of navigation including their orientations and if they are measurable or not.

More specifically, while the above target may normally be a patient, a tumor to be surgically treated of a patient or an area of the body of a patient requiring special attention during a surgical operation, it is by no means limited to an existing object of examination and may alternatively be a virtual target displayed as a two-dimensional or three-dimensional image of a model synthesized by using the video information of an existing target that is obtained in advance.

While the above object may normally refer to an endoscope 3, it may alternatively refer to some other surgical instrument such as a suction pipe or a pair of forceps.

While the above three-dimensional position and orientation measuring section refers to sensors using LEDs for emitting infrared rays (sensing plates 2, 4, sensor assembly 7, sensor information storage section 5 and sensor control section 6), it may alternatively refer to a sensing system using magnetic sensors or a sensing system using a set of mechanical links and joints, an encoder and a potentiometer popularly used in ordinary three-dimensional position and orientation measuring systems.

The computational information determining section refers to the navigation-related information storage section 9 and the navigation-related information control section 8.

While the information display section refers to the liquid crystal monitor 13, it may alternatively refer to some other video information display such as a CRT display or a head mount display.

The expression "attributes of navigation-related information" as used herein refers to the color, the thickness of line, the dimensions the drawing and the density of drawing lines.

With a navigation apparatus according to another aspect of the present invention, the navigation-related information includes a model image of the profile of the target and/or that of the object of navigation, a model image of the internal tomographic information of the target, a symbol pattern indicating the direction in which the target and/or the object of navigation will be found and/or a numerical value ○ a symbol pattern indicating the distance between the target and the object of navigation when the three-dimensional position and orientation measuring section is operating normally.

When the three-dimensional position and orientation measuring section is inoperative, the navigation-related information refers to character information or a symbol pattern indicating that the three-dimensional position and orientation measuring section is in operative.

More specifically, while the above model image of the profile refers to wireframe model data 10 in the first embodiment, it may also refer to model data adapted to express a profile, including a popular data structure to be used for three-dimensional computer graphics.

Additionally, while it refers to the lines drawing the orthogonal projection image 27 of the endoscope 3 in the second embodiment, it may also refer to expression techniques adapted to express a profile, including a popular data structure to be used for three-dimensional computer graphics.

Still additionally, while the model image of the internal tomographic information refers to the three-dimensional volume data 11 of the target area in the first and second embodiments, it may alternatively take a form where a plurality of two-dimensional pixel data exist.

While the above described symbol pattern indicating the direction in which the object of navigation will be found refers to the arrow 21 in the first embodiment, it may alternatively be a two-dimensional geometric figure such as a triangle or a circle, a three-dimensional geometric figure such a cone or a set of visually recognizable image data.

While the above described numerical value indicating the distance to the target refers to the numeral 31 indicating the distance to the tumor in the first embodiment, it may alternatively be a numeral indicating the distance to an appropriate target.

While it also refers to the bar 30 indicating the distance to the tumor in the first embodiment, it may alternatively be a two-dimensional geometric figure such as a triangle or a circle, a three-dimensional geometric figure such a cone or a set of visually recognizable image data.

While the character information indicating an unmeasurable condition refers to the character information 28 of "unmeasurable condition" in the first embodiment, it may alternatively include any character information telling the user that the apparatus is in an unmeasurable condition.

While it also refers to a yellow pixel frame 29 having a width equal to 60 pixels in the first embodiment, it may alternatively refer to any expression using symbols defined to indicate an unmeasurable condition.

With a navigation apparatus according to another aspect of the present invention, the object of navigation has an observational function and the observed image obtained by means of the observational function is displayed with other navigation-related information obtained by the computational information determining section in an overlaid manner.

Thus, the user can obtain an actual image of the object and navigation-related information simultaneously and hence comprehend the position, the profile and the condition of the object that he or she cannot see on the basis of the navigation-related information.

While the object of navigation having an observational function refers to the endoscope 3 in the first embodiment, it may alternatively refer to a microscope or some other object.

While the above information display section normally refers to the liquid crystal monitor 13 in the first embodiment, it may alternatively refer to some other video information display such as a CRT display or a head mount display.

With a navigation apparatus according to another aspect of the present invention, the navigation-related information displayed on the display section changes its color as a function of the relative distance between the target and the object as measured by the three-dimensional position and orientation measuring section so that the user can visually comprehend with ease a situation where the relative distance is made too small.

Alternatively, it may be so arranged that the navigation-related information displayed on the display section changes its color as a function of the relative direction of the target and the object of navigation so that the user also can visually comprehend a situation where the relative direction is deviated from the right direction.

Still alternatively, the color may be made to change simultaneously as a function of both the relative distance and the relative direction. Then, the user can visually comprehend both the relative distance and the direction with ease.

More specifically, while the color of the displayed navigation-related information refers to that of the wireframe image 18 of the target area and the internal tomographic image 19 displayed on the monitor in the first embodiment, it may also refer to the color of the arrow 21 of the first embodiment.

It may additionally refers to the color of the tri-sectional image 26 of the target area and the orthogonal projection image 27 of the endoscope 3 in the second embodiment.

With a navigation apparatus according to another aspect of the present invention, the thickness of the lines of the navigation-related information obtained by the three-dimensional position and orientation measuring section is made to vary as a function of the relative distance between the target and the object of navigation so that the user can visually comprehend with ease a situation where the relative distance has become too small.

Alternatively, it may be so arranged that the thickness of the lines of the navigation-related information vary as a function of the direction to the target as viewed from the object of navigation so that the user can also visually comprehend with ease a situation where the relative direction has deviated.

While the thickness of the lines of navigation-related information refers to the wireframe image 18 of the target area drawn on the monitor in the first embodiment, it may also include the arrow 21 in the first embodiment.

It refers to the orthogonal projection image 27 of the endoscope 3 drawn on the monitor in the second embodiment.

With a navigation apparatus according to another aspect of the present invention, the profile model of the target and the internal tomographic image are switched from one to the other on the display section as a function of the relative distance between the target and the object as measured by the three-dimensional position and orientation measuring section so that the user can visually comprehend with ease that the object is located close to the target.

Thus, the user can get necessary information with ease depending on if the distance between the object and the target is smaller than a predetermined value or not.

More specifically, while the above profile model refers to wireframe image 18 in the first embodiment, it may also refer to various profiles used in three-dimensional computer graphics such as polygon as well as contour lines and equidistant curves drawn relative to the viewing direction.

The above internal tomographic image refers to the internal tomographic image 19 of the first embodiment.

With a navigation apparatus according to another aspect of the present invention, the density of lines drawing the target model image is finely lowered when the relative distance between the target and the object is large and finely raised when the relative distance is small so as to make the load of drawing the target image and the quantity of information used for displaying the image may be well balanced.

As a result, the user can obtain an adequate amount of information that is displayed with an adequate drawing rate depending as a function of the relative distance between the target and the object.

More specifically, while the above profile model refers to wireframe image 18 in the first embodiment, it may also refer to various profiles used in three-dimensional computer graphics such as polygon as well as contour lines and equidistant curves drawn relative to the viewing direction.

With a navigation apparatus according to another aspect of the present invention, the computational information determining section computationally determines the positional relationship of the image to be displayed and the display area of the display section on the basis of the relative distance between the target and the object of navigation and the relative direction of the target as viewed from the object and only a symbol pattern is displayed when no model image is displayed in the display area so that the user can comprehend the relative positions of the target and the object and the direction of the target as viewed from the object without missing either of them by selecting the display of the direction when no image is displayed for the target.

More specifically, while the above profile model refers to wireframe image 18 in the first embodiment, it may also refer to various profiles used in three-dimensional computer graphics such as polygon as well as contour lines and equidistant curves drawn relative to the viewing direction along with information on the internal tomographic image.

While the above described symbol pattern refers to the arrow 21 in the first embodiment, it may alternatively be a two-dimensional geometric figure such as a triangle or a circle, a three-dimensional geometric figure such a cone or a set of visually recognizable image data.

With a navigation apparatus according to another aspect of the present invention, the relative distance between the target and the object is indicated by the size of a pattern so that the user can visually comprehend with ease not only the distance but also the direction of the target as viewed from the object.

More specifically, while the above described symbol pattern refers to the arrow 21 in the first embodiment, it may alternatively be a two-dimensional geometric figure such as a triangle or a circle, a three-dimensional geometric figure such a cone or a set of visually recognizable image data.

As described above, both the above described first and second embodiments of navigation apparatus according to the invention are adapted to modify the navigation-related information displayed on the display section as a function of the relative three-dimensional positions and orientations of the target and the object of navigation to make the user easily comprehend the distance between the target and the object and obtain navigation-related information of necessary type with ease.

Now, the third and fourth embodiments of the invention will be described. They are surgical operation image acquisition/display apparatus realized by applying a navigation apparatus according to the invention.

Embodiment 3

Figure 14:
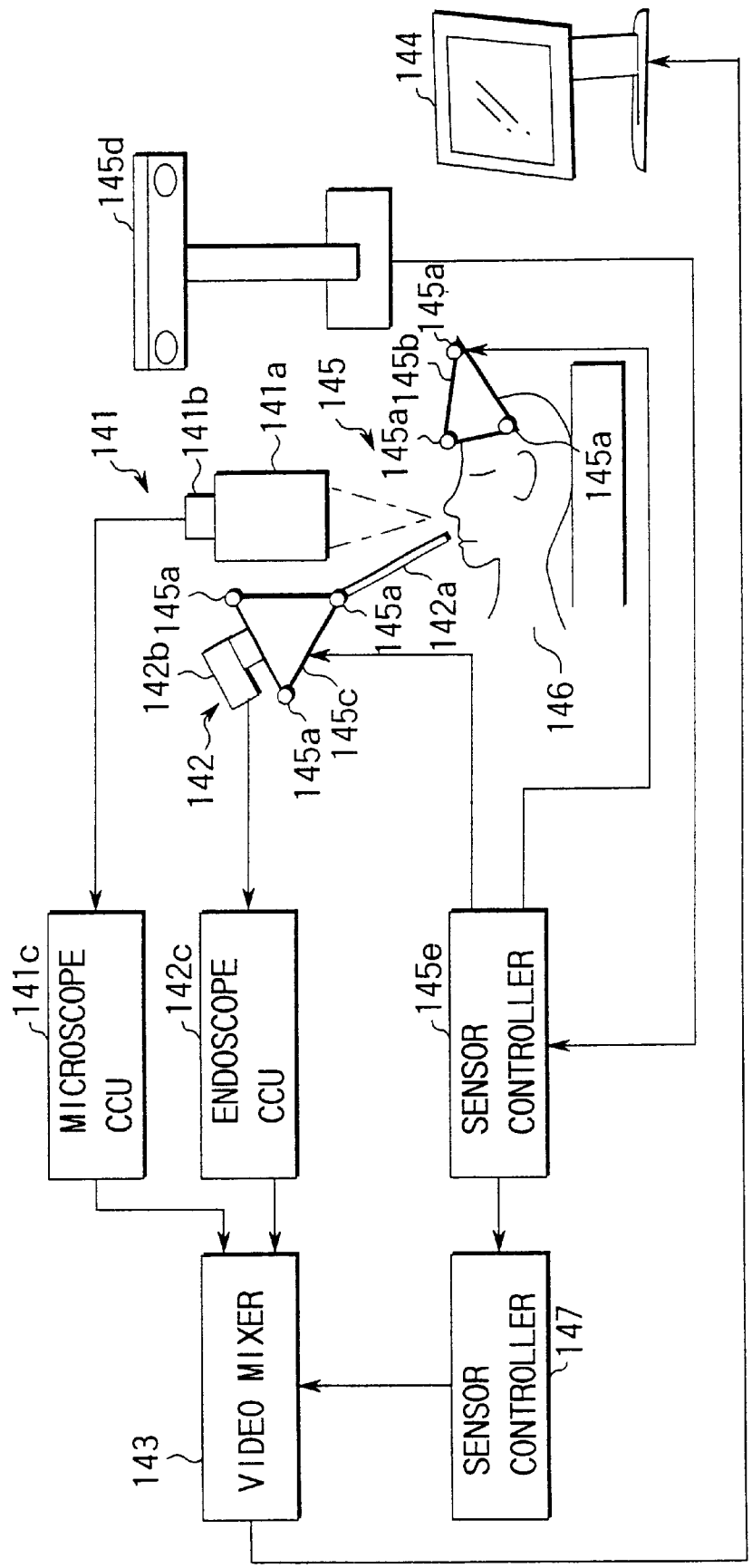
FIG. 14 is a schematic block diagram of the third embodiment of the invention which is a surgical operation image acquisition/display apparatus, showing its configuration.

FIG. 14 is a schematic block diagram of the third embodiment of the invention which is a surgical operation image acquisition/display apparatus, showing its configuration; The third embodiment of surgical operation image acquisition/display apparatus according to the invention has a configuration as described below.

Referring to FIG. 14, the surgical operation image acquisition/display apparatus comprises a surgical microscope 141 (first observation section) and an endoscope 142 (second observation section) for observing an area located in the dead angle of the surgical microscope 141.

The surgical microscope 141 includes an microscope optical system 141a mounted on a stand (not shown), a microscope camera 141b attached to the microscope optical system 141a and a microscope camera control unit (hereinafter referred to as microscope CCU) 141c for converting the output of the microscope camera 141b into a video signal.

The microscope optical system 141a is provided with illumination light emitted from a light source (not shown) and guided by a light guide (not shown) for the purpose of observation.

On the other hand, the endoscope 142 includes an endoscope optical system 142a, an endoscope camera 142b attached to the endoscope optical system 142a and an endoscope camera control unit (hereinafter referred to as endoscope CCU) 142 for converting the output of the endoscope camera into a video signal.

The endoscope optical system 142a is provided with illumination light emitted from a light source (not shown) and guided by a light guide (not shown) for the purpose of observation.

The video output of the microscope CCU 141c and that of the endoscope CCU 142c are fed to a video mixer 143 (observed image synthesizing section).

As illustrated in FIGS. 15A through 15F, the video mixer 143 has a plurality of display modes 0 through 5.

In the display mode 0 (FIG. 15A), the video output of the microscope CCU 141c is displayed without being processed.

In the display mode 1 (FIG. 15B), the video output of the endoscope CCU 142c is displayed without being processed.

In the display mode 2 (FIG. 15C), the video output of the endoscope CCU 142c is dimensionally reduced and displayed in the video output of the microscope CCU 141c.

In the display mode 3 (FIG. 15D), the video output of the microscope CCU 141c is dimensionally reduced and displayed in the video output of the endoscope CCU 142c.

The extent of dimensional reduction and the display position of the dimensionally reduced output are variable both in the display mode 2 and the display mode 3.

In the display mode 4 (FIG. 15E), which is a variation of the display mode 2 and in which the video output of the endoscope CCU 142c is dimensionally reduced and displayed at the right top corner of the video output of the microscope CCU 141c, the video output of the endoscope CCU 142c is dimensionally reduced to the same extent and displayed at the left bottom corner of the video output of the microscope CCU 141c.

Similarly, in the display mode 5 (FIG. 15F), which is a variation of the display mode 3 and in which the video output of the microscope CCU 141c is dimensionally reduced and displayed at the right top corner of the video output of the endoscope CCU 142c, the video output of the microscope CCU 141c is dimensionally reduced to the extent smaller than that of FIG. 15D and displayed at the right top corner of the video output of the endoscope CCU 142c.

The mode of display and the position and the size of the displayed image (or each of the displayed images) as defined by the video mixer 143 can be appropriately changed by means of an externally applied control signal. More specifically, the displayed image(s) can be enlarged or reduced independently with an appropriately selected magnification factor.

Then, the output of the video mixer 143 is fed to a liquid crystal display 144 (display section) and displayed to the surgical operator for observation.

The combination of the video mixer 143 and the liquid crystal display 144 corresponds to the image display section as used in the appended claims.

Referring to FIG. 14, position and orientation sensor 145 (position and orientation detection section) comprises hard sensing plates 145b and 145c, each having three infrared light emitting diodes (LEDs) 145a for emitting arranged at the respective corners of a triangle, a sensor assembly 145d for detecting the quantity of light emitted from each of the infrared LEDs 145a for emitting and a sensor controller 145e for computationally determining the three-dimensional position and orientation of the sensing plate 145b and that of the sensing plate 145c from the output of the sensor assembly.

Note that the position of each of the LEDs 145a for emitting infrared is observed and determined in advance in terms of the coordinate system defined on each of the sensing plates 145b and 145c and stored in the sensor controller 145e as LED definition data.

Assume that the sensing plate 145b is attached to the head of the patient 146 in such a way that its position and orientation relative to the head would not change easily.

The other sensing plate 145c is attached to the endoscope 143 by a mount section (not shown).

The sensor controller 145e is connected to an image controller 147 (state of synthesis modification specifying section).

The image controller 147 is connected to the video mixer 143.

Assume that the area of operation to be surgically treated and certain characteristic points on the patient are observed by means of CT or MRI and the three-dimensional positions thereof are computationally determined by an image processing computer (not shown) and stored in the image controller 147 as data on the area and the characteristic points.

Figure 16:
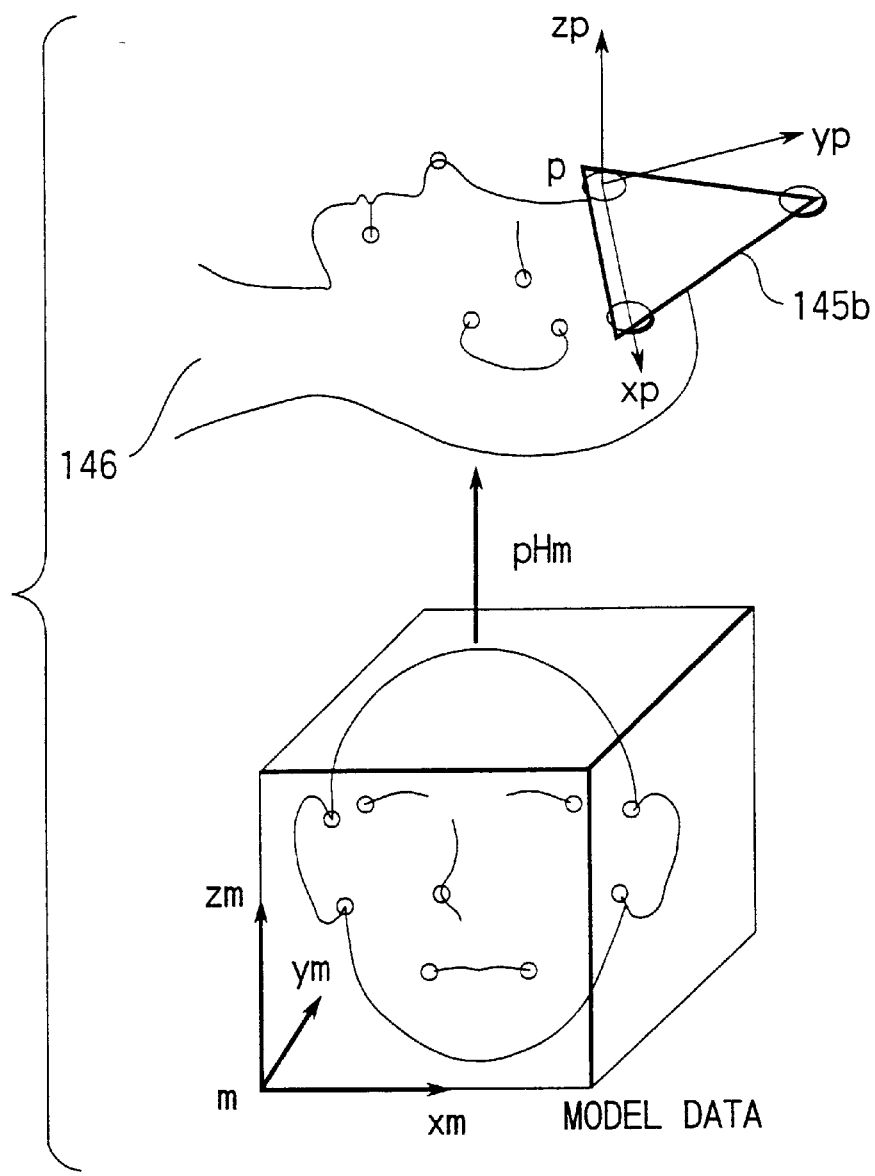
FIG. 16 is a schematic illustration of an operation of correlating data on the operation area of a patient 146 and data on the characteristic points of a model data coordinate system m.
Figure 17:
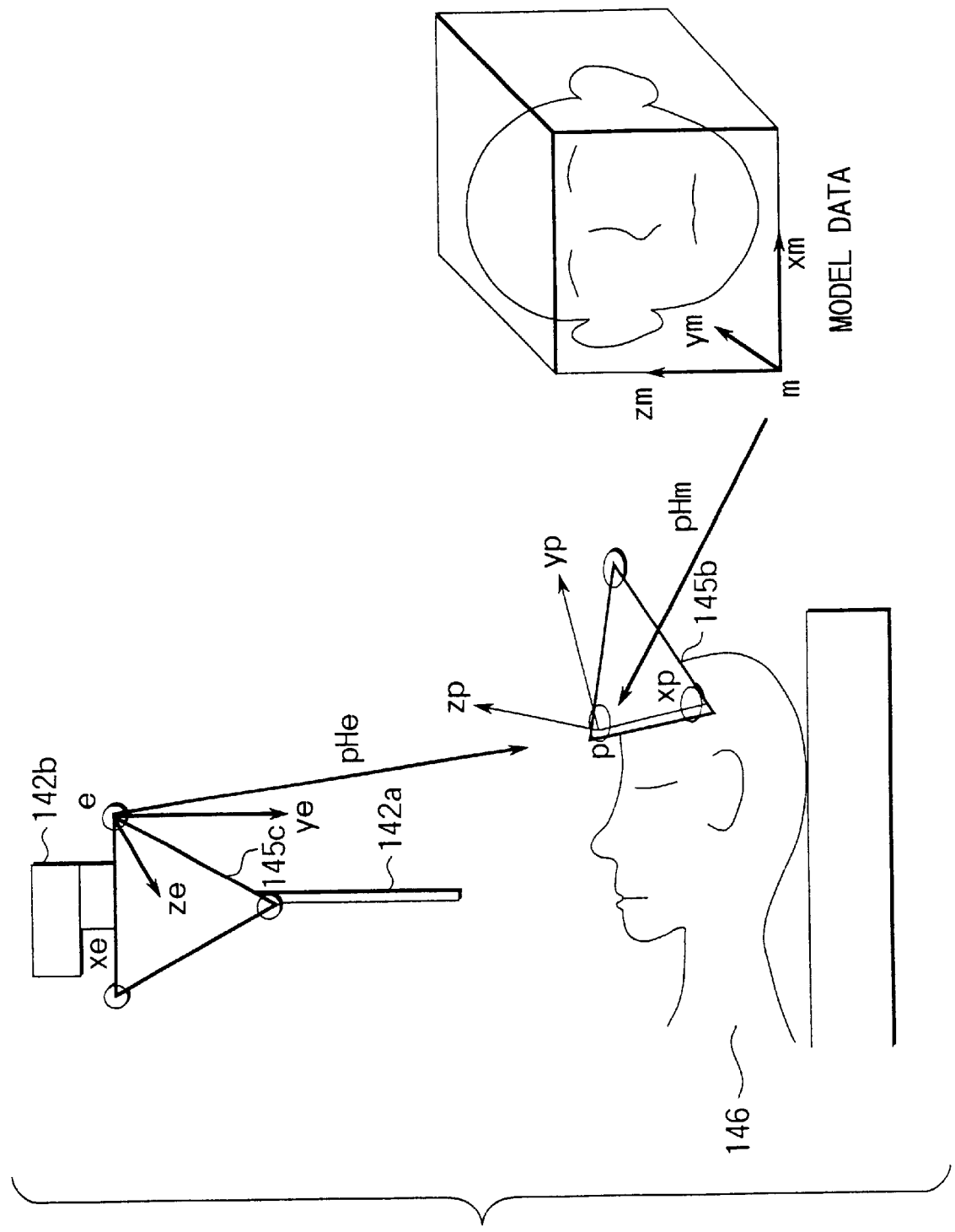
FIG. 17 is a schematic illustration of a mode of computationally obtaining a coordinate transformation matrix pHe for transforming the patient coordinate system p defined by the sensing plate 145b fitted to the head of a patient 146 to the endoscope coordinate system e defined by the sensing plate 145c fitted to an endoscope 142.

At this time, as shown in FIG. 16, the data on the area of surgical operation and the patient 146 are correlated by observing the coordinate values of the characteristic points in the model data coordinate system m and those of the characteristic points on the patient 146 in the patient coordinate system p defined by the sensing plate 145b and computing a coordinate transformation matrix pHm.

The coordinate transformation matrix pHm is stored in the storage section of the image controller 147.

Similarly, the coordinate values of the front end and those of the rear end of the endoscope 142 are observed in terms of the endoscope coordinate system e defined by the sensing plate 145c attached to the endoscope 142 and stored in the storage section of the image controller 147.

Now, the operation of the third embodiment will be described below.

When the surgical operation image acquisition/display apparatus is used, the surgical microscope 141 and the endoscope 142 are combined for use as shown in FIG. 14.

When the surgical operation image acquisition/display apparatus is in operation, the sensor controller 145e drives the infrared LEDs 145a to sequentially emit and determines the three-dimensional position of each of the infrared LEDs 145a on the basis of its output. At the same time, the sensor controller 145e computationally determines the three-dimensional Position and orientation of the sensing plate 145b and that of the sensing plate 145c, using the LED definition data stored in the sensor controller 145e and outputs the obtained data to the image controller 147 upon request.

The image controller 147 computes the coordinate transformation matrix pHe from the sensing plate 145bof the patient coordinate system p attached to the head of the patient 146 to the sensing plate 145c of the endoscope coordinate system e attached to the endoscope 142 on the basis of the three-dimensional position and orientation information.

The image controller 147 also computationally determines the relative distance between the patient 146 and the endoscope 142 and the relative direction of the patient 146 as viewed from the endoscope 142 on the basis of the coordinate transformation matrix pHe and the above described coordinate transformation matrix pHm.

Figure 18:
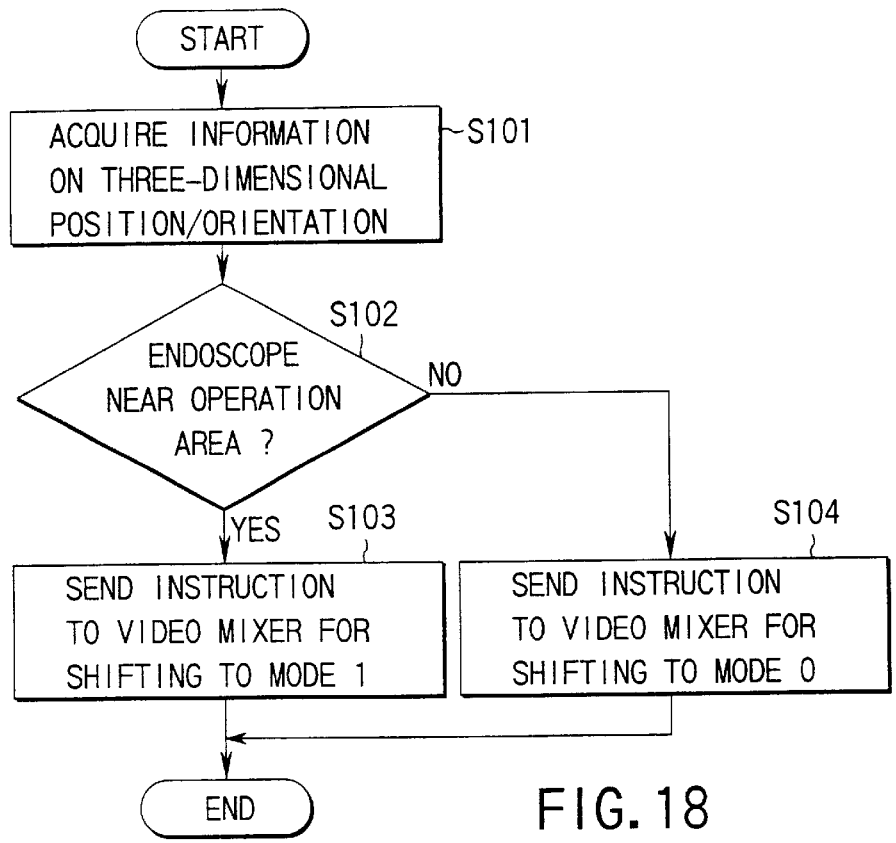
FIG. 18 is a flow chart of the operation of the image controller 147 of FIG. 14.

The processing operation of the image controller 147 will be described further by referring to the flow chart of FIG. 18.

Firstly, the image controller 147 outputs a request signal cyclically with a predetermined period (e.g., 33 msec) to the sensor controller 145e to receive the three-dimensional position and orientation information on the sensing plates 145b and 145c from the sensor controller 145e (Step S101).

Then, the image controller 147 judges if the endoscope 142 is located close to the area of surgical operation (e.g., within a range of 50 mm) on the basis of the received three-dimensional position and orientation information (Step S102).

If the image controller 147 judges that the endoscope 142 is located close to the area of surgical operation, it outputs an instruction for switching from the microscope image to the endoscope image (mode 1) to the video mixer 143 (Step S103).

If, on the other hand, the image controller 147 judges that the endoscope 142 is not located close to the area of surgical operation, it outputs an instruction for switching from the endoscope image to the microscope image (mode 0) to the video mixer 143 (Step S104).

When, the endoscope 142 is moved away from the area of surgical operation and the area is observed mainly by the surgical microscope 141 as a result of the above judgment, the image observed through the surgical microscope 141 is displayed on the liquid crystal display 144. On the other hand, when the endoscope 142 is moved closer to the area of surgical operation, the image observed through the endoscope 142 is displayed on the liquid crystal display 144.

Because the image observed through the surgical microscope is displayed on the liquid crystal display 144 when the endoscope 142 is moved away from the area of surgical operation, the surgeon can see the desired image without paying effort for switching from the microscope image to the endoscope image.

It may be needless to say that the configuration of this embodiment can be modified and/or altered in various different ways without departing from the scope of the invention.

For instance, while the first observation section refers to the surgical microscope 141 in this embodiment, it may alternatively be the endoscope 142 or some other observation sections or units.

While the second observation section refers to the endoscope 142 in this embodiment, it may alternatively be the surgical microscope 141 or some other observation sections or units.

While the image synthesizing section refers to the video mixer 143 in this embodiment, it may be some other section for externally modifying the synthesized state of a plurality of images.

While the display section refers to the liquid crystal display 144 in this embodiment, it may alternatively be a CRT display, a head mounted display or a projector adapted to display video signals.

While the position and orientation detection section is the position and orientation sensor (comprising the infrared LEDs 145a for emitting, the sensing plates 145b, 145c, the sensor assembly 145d and the sensor controller 145e) in this embodiment, it may alternatively be any appropriate section for detecting the three-dimensional position and orientation of an object such as a magnetic sensor or a set of mechanical links and joints, encoders and potentiometers.

While the state of synthesis modification specifying section of this embodiment uses the distance between the area of surgical operation and the endoscope 142 for its judgment, it may alternatively use both the distance and the direction of the area as viewed from the endoscope 142.

While the position and orientation detection section of this embodiment detects the position and orientation of the endoscope 142, it may alternatively detect the position and orientation of the microscope 141 or both the position and orientation of the endoscope 142 and that of the microscope 141.

Embodiment 4

Now, the fourth embodiment of the invention, which is also a surgical operation image acquisition/display apparatus, will be described below.

The fourth embodiment of surgical operation image acquisition/display apparatus has a configuration substantially same as the above described third embodiment and hence the similar components in the graphic illustrations thereof will be denoted respectively by the same reference symbols and will not be described any further.

Additionally, since the operational function of the fourth embodiment of surgical operation image acquisition/display apparatus is same as that of the above described third embodiment except the processing operation of the image controller 147, only the latter will be discussed hereinafter.

More specifically, in this embodiment, one of the obtained two images is dimensionally reduced and synthetically combined with the other image so that they may be displayed simultaneously on the display screen for observation.

Figure 19:
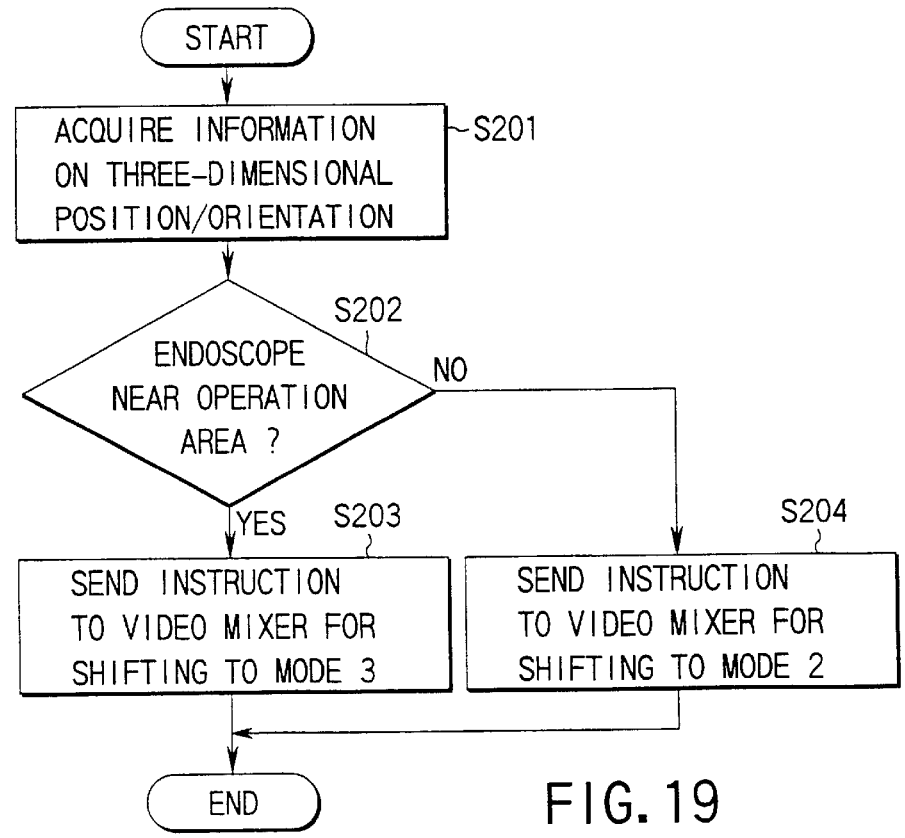
FIG. 19 is a flow chart of the operation of the image controller 147 of the fourth embodiment of the invention which is also a surgical operation image acquisition/display apparatus.

The processing operation of the image controller 147 will be discussed below by referring to the flow chart of FIG. 19.

Firstly, the image controller 147 outputs a request signal cyclically with a predetermined period (e.g., 33 msec) to the sensor controller 145e to receive the three-dimensional position and orientation information on the sensing plates 145b and 145c from the sensor controller 145e (Step S201).

Then, the image controller 147 judges if the endoscope 142 is located close to the area of surgical operation (e.g., within a range of 50 mm) on the basis of the received three-dimensional position and orientation information (Step S202).

If the image controller 147 judges that the endoscope 142 is located close to the area of surgical operation, it outputs an instruction for dimensionally reducing the microscope image and display it with the endoscope image (mode 3) to the endoscope image (mode 1) to the video mixer 143 (Step S203).

If, on the other hand, the image controller 147 judges that the endoscope 142 is not located close to the sit of surgical operation, it outputs an instruction for dimensionally reducing the endoscope image and display it with the microscope image (mode 2) to the video mixer 143 (Step S204).

When, the endoscope 142 is moved away from the area of surgical operation and the area is observed mainly by the surgical microscope 141 as a result of the above judgment, the dimensionally reduced image observed through the endoscope 142 is displayed with the image observed through the surgical microscope 141 on the liquid crystal display 144.

On the other hand, when the endoscope 142 is moved closer to the area of surgical operation, the dimensionally reduced image observed through the surgical microscope 141 is displayed with the image observed through the endoscope 142 on the liquid crystal display 144.

Because the dimensionally reduced image observed through the endoscope 142 is displayed with the image observed through the surgical microscope on the liquid crystal display 144 when the endoscope 142 is moved away from the area of surgical operation, the surgeon can see the desired plurality of images without paying effort for switching from the microscope image to the endoscope image.

It may be needless to say that the configuration of this fourth embodiment can be modified and/or altered in various different ways without departing from the scope of the invention.

For instance, while the first observation section refers to the surgical microscope 141 in these embodiments, it may alternatively be the endoscope 142 or some other observation sections or units.

While the second observation section refers to the endoscope 142 in these embodiments, it may alternatively be the surgical microscope 141 or some other observation sections or units.

While the image synthesizing section refers to the video mixer 143 in these embodiments, it is by no means limited thereto and may be some other section for externally modifying the synthesized state of a plurality of images.

While the display section refers to the liquid crystal display 144 in these embodiments, it may alternatively be a CRT display, a head mounted display or a projector adapted to display video signals.

While the position and orientation detection section is the position and orientation sensor (comprising the infrared LEDs 145a for emitting, the sensing plates 145b, 145c, the sensor assembly 145d and the sensor controller 145e) in these embodiments, it may alternatively be any appropriate section for detecting the three-dimensional position and orientation of an object such as a magnetic sensor or a set of mechanical links and joints, encoders and potentiometers.

The state of synthesis modification specifying section refers to the image controller in these embodiments.

As described above, both the third and fourth embodiments of the invention provide a surgical operation image acquisition/display apparatus that efficiently assists a surgeon to smoothly carry out a surgical operation without requiring him or her to switch the observation system from one to another by means of a navigation apparatus when the surgical operation is conducted by using a plurality of observation systems including a surgical microscope and an endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical operation image acquisition/display apparatus comprising:

a first observation section for observing an area of a surgical operation;

a second observation section, whose position can be changed, also for observing the area of the surgical operation;

a position detection section for detecting a position of the second observation section;

a specifying section for specifying an image to be displayed according to an output of the position detection section, wherein the specifying section specifies: (i) an image observed by the second observation section when the second observation section is located close to the area of the surgical operation, and (ii) an image observed by the first observation section when the second observation section is not located close to the area of the surgical operation; and an image display section for displaying the image specified by the specifying section.

2. A surgical operation image acquisition/display apparatus according to claim 1, wherein the specifying section judges the second observation section as being located close to the area of the surgical operation when a distance between the second observation section and the area of the surgical operation is within a predetermined range.

3. A surgical operation image acquisition/display apparatus according to claim 1, wherein the position detection section is configured to observe an area located in a dead angle of the first observation section.

4. A surgical operation image acquisition/display apparatus according to claim 1, wherein the second observation section is configured to observe an area located in a dead angle of the first observation section.

5. A surgical operation image acquisition/display according to claim 1, wherein the first observation section comprises a surgical microscope.

6. A surgical operation image acquisition/display apparatus according to claim 1, wherein the second observation section comprises an endoscope.

7. A surgical operation image acquisition/display apparatus comprising:

a first observation section for observing an area of a surgical operation;

a second observation section, whose position can be changed, also for observing the area of the surgical operation;

a position detection section for detecting a position of the second observation section;

an image synthesizing section, operable in a plurality of modes, for synthesizing an image observed by the first observation section and an image observed by the second observation section to produce a synthesized image;

a specifying section for specifying one of the plurality of modes of the image synthesizing section according to an output of the position detection section, wherein the specifying section specifies: (i) a first mode in which the image observed by the second observation section is allocated to an area larger than that of the image observed by the first observation section in the synthesized image when the second observation section is located close to the area of the surgical operation, and (ii) a second mode in which the image observed by said first observation section is allocated to an area larger than that of the image observed by the second observation section in the synthesized image when the second observation section is not located close to the area of the surgical operation; and an image display section for displaying the synthesized image.

8. A surgical operation image acquisition/display apparatus according to claim 7, wherein the specifying section judges the second observation section as being located close to the area of the surgical operation when a distance between the second observation section and the area of the surgical operation is within a predetermined range.

9. A surgical operation image acquisition/display apparatus according to claim 7, wherein the position detection section also detects an orientation of the second observation section.

10. A surgical operation image acquisition/display apparatus according to claim 7, wherein the second observation section is configured to observe an area located in a dead angle of the first observation section.

11. A surgical operation image acquisition/display apparatus according to claim 7, wherein the first observation section comprises a surgical microscope.

12. A surgical operation image acquisition/display apparatus according to claim 7, wherein the second observation section comprises an endoscope.

13. A surgical operation image acquisition/display apparatus comprising:

a first observation section for observing an area of a surgical operation;

a second observation section, whose position can be changed, also for observing the area of the surgical operation;

a position detection section for detecting a position of the second observation section;

an image display section for displaying an image; and a specifying section for specifying one of the first and second observation sections as a main image source of the image displayed on the image display section according to an output of the position detection section, wherein the specifying section specifies: (i) the second observation section when the second observation section is located close to the area of the surgical operation, and (ii) the first observation section when the second observation section is not located close to the area of the surgical operation.

14. A surgical operation image acquisition/display apparatus comprising:

first observation means for observing an area of a surgical operation;

second observation means, whose position can be changed, also for observing the area of the surgical operation;

position detection means for detecting a position of the second observation means;

specifying means for specifying an image to be displayed according to an output of the position detection means, wherein the specifying means specifies: (i) an image observed by the second observation means when the second observation means is located close to the area of the surgical operation, and (ii) an image observed by the first observation means when the second observation means is not located close to the area of the surgical operation; and image display means for displaying the image specified by the specifying means.

15. A surgical operation image acquisition/display apparatus comprising:

first observation means for observing an area of a surgical operation;

second observation means, whose position can be changed, also for observing the area of the surgical operation;

position detection means for detecting a position of the second observation means;

image synthesizing means, operable in a plurality of modes, for synthesizing an image observed by the first observation means and an image observed by the second observation means to produce a synthesized image;

specifying means for specifying one of the plurality of modes of the image synthesizing means according to an output of the position detection means, wherein the specifying means specifies: (i) a first mode in which the image observed by the second observation means is allocated to an area larger than that of the image observed by the first observation means in the synthesized image when the second observation means is located close to the area of the surgical operation, and (ii) a second mode in which the image observed by said first observation means is allocated to an area larger than that of the image observed by the second observation means in the synthesized image when the second observation means is not located close to the area of the surgical operation; and image display means for displaying the synthesized image.

* * * * *